(12) United States Patent
Ohashi

(10) Patent No.: US 7,908,026 B2
(45) Date of Patent: Mar. 15, 2011

(54) APPARATUS FOR TESTING DEFECTS OF SHEET-SHAPED PRODUCT HAVING OPTICAL FILM, APPARATUS FOR PROCESSING TEST DATA THEREOF, APPARATUS FOR CUTTING THE SAME, AND PRODUCTION THEREOF

(75) Inventor: Hiromichi Ohashi, Ibaraki (JP)

(73) Assignee: NITTO DENKO CORPORATION, Ibaraki-shi, Osaka (JP)

(*) Notice: Subject to any disclaimer, the term of this patent is extended or adjusted under 35 U.S.C. 154(b) by 455 days.

(21) Appl. No.: 11/870,082

(22) Filed: Oct. 10, 2007

(65) Prior Publication Data

US 2008/0087149 A1 Apr. 17, 2008

(30) Foreign Application Priority Data

Oct. 11, 2006 (JP) ................................. 2006-277916
Jul. 12, 2007 (JP) ................................. 2007-183468

(51) Int. Cl.
*G06F 19/00* (2011.01)
*G01N 37/00* (2006.01)

(52) U.S. Cl. ............. 700/122; 700/121; 702/81; 702/82; 702/83; 702/84

(58) Field of Classification Search ........................ None
See application file for complete search history.

(56) References Cited

U.S. PATENT DOCUMENTS

| | | | |
|---|---|---|---|
| 3,202,043 A | 8/1965 | Galey et al. | |
| 3,652,863 A | 3/1972 | Gaskell et al. | |
| 5,450,201 A * | 9/1995 | Katzir et al. | 356/369 |
| 5,459,576 A * | 10/1995 | Brunfeld et al. | 356/520 |
| 6,650,410 B2 * | 11/2003 | Shimoda | 356/239.1 |
| 7,079,245 B2 * | 7/2006 | Kurata et al. | 356/364 |
| 7,641,837 B2 * | 1/2010 | Takiyama et al. | 264/284 |
| 2002/0154308 A1 * | 10/2002 | Uesugi et al. | 356/431 |
| 2003/0031848 A1 * | 2/2003 | Sawada et al. | 428/220 |
| 2003/0184722 A1 * | 10/2003 | Kyusho | 355/55 |
| 2004/0095526 A1 * | 5/2004 | Yamabuchi et al. | 349/96 |

(Continued)

FOREIGN PATENT DOCUMENTS

GB 1526930 10/1978

(Continued)

OTHER PUBLICATIONS

European Search report dated Mar. 1, 2010, issued in corresponding European Patent Application No. 07117918.

(Continued)

*Primary Examiner* — Albert Decady
*Assistant Examiner* — Sunray R Chang
(74) *Attorney, Agent, or Firm* — Westerman, Hattori, Daniels & Adrian, LLP

(57) ABSTRACT

A defect testing apparatus for testing defects of optical film sheet-shaped product of an optical displaying apparatus, which includes a defect detecting means for detecting defects of a monolayer body and/or a laminate body constituting the sheet-shaped product in a state in which a protective layer on a surface of the sheet-shaped product is not disposed and defect information preparing means for preparing defect information which is information related to the defects detected by the defect detecting means, and the defect information is used for producing the sheet-shaped product provided in a roll form or in separate sheets.

3 Claims, 12 Drawing Sheets

U.S. PATENT DOCUMENTS

| | | | |
|---|---|---|---|
| 2006/0037693 A1* | 2/2006 | Wade | 156/234 |
| 2006/0164647 A1* | 7/2006 | Shibata | 356/430 |
| 2006/0203246 A1 | 9/2006 | Nakajima et al. | |
| 2008/0088790 A1* | 4/2008 | Ohashi | 349/192 |
| 2009/0280411 A1* | 11/2009 | Ohira et al. | 429/221 |

FOREIGN PATENT DOCUMENTS

| | | |
|---|---|---|
| GB | 2173294 A | 10/1986 |
| JP | 2003-149164 A | 5/2003 |
| JP | 2005-9919 A | 1/2005 |
| JP | 2005-62165 A | 3/2005 |
| WO | 2005-065367 A2 | 7/2005 |

OTHER PUBLICATIONS

European Serach Report dated Dec. 23, 2009, issued in corresponding European Patent Application No. 07117918.

* cited by examiner

[FIG.1]
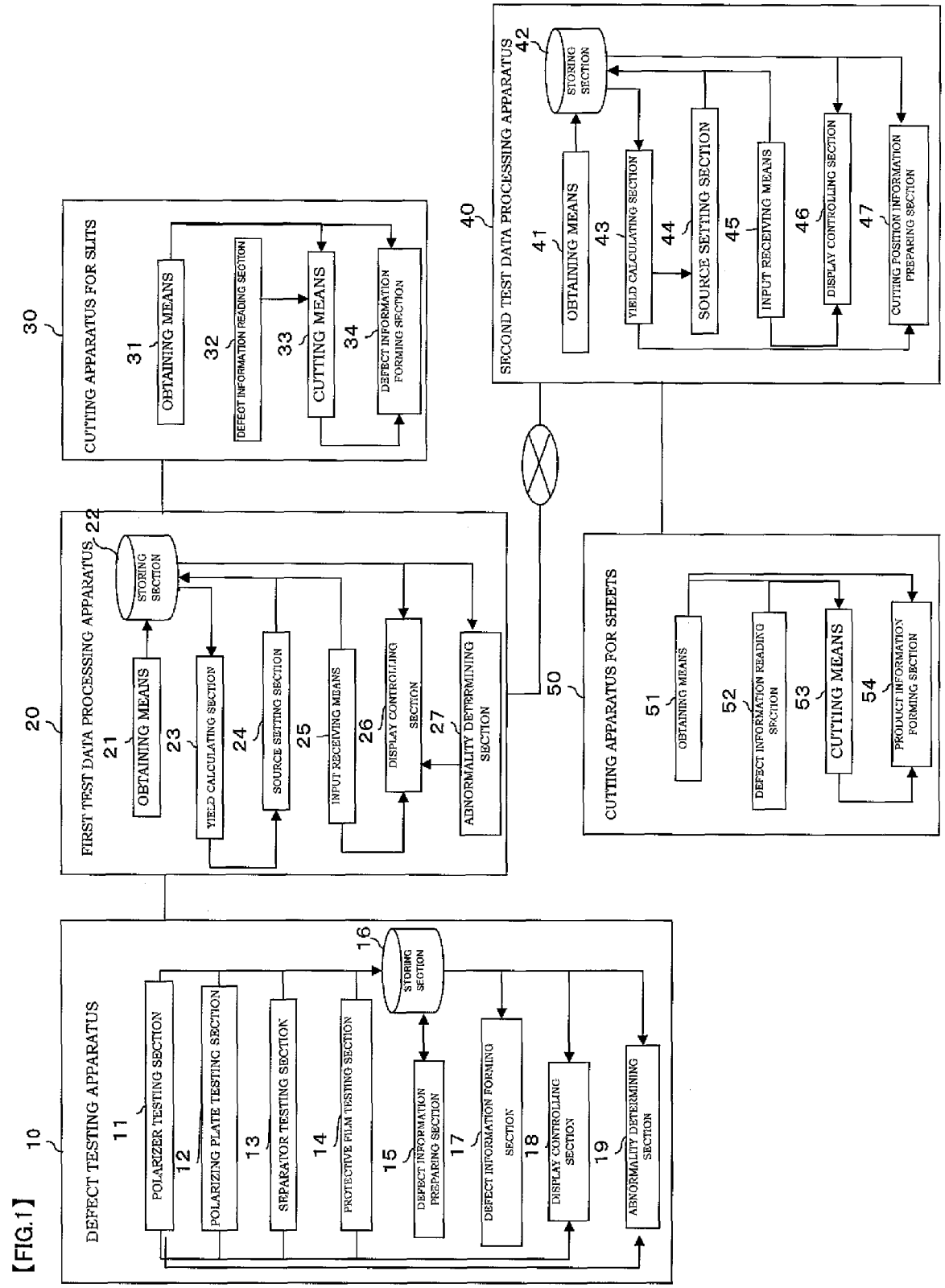

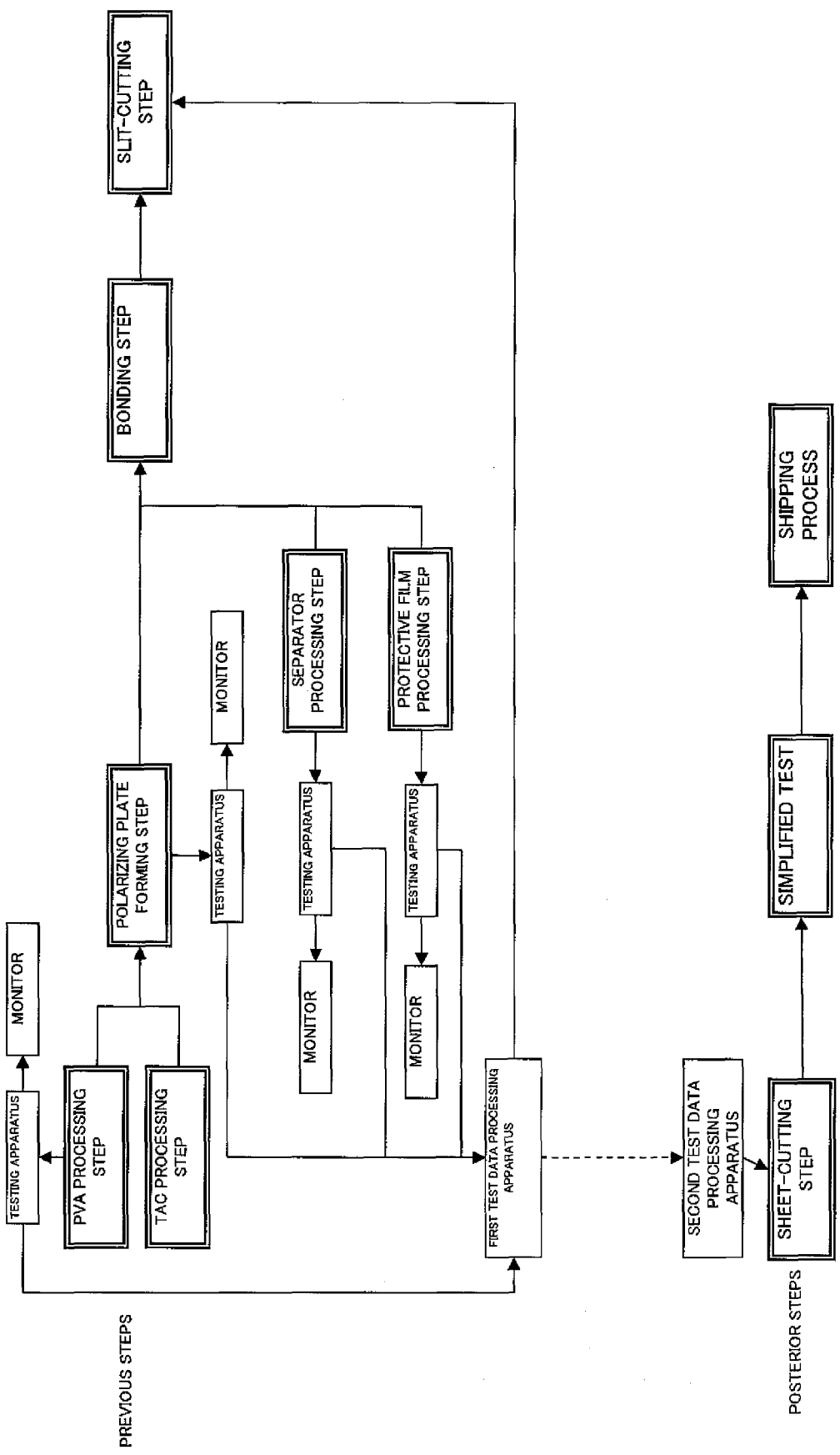
[FIG.2]

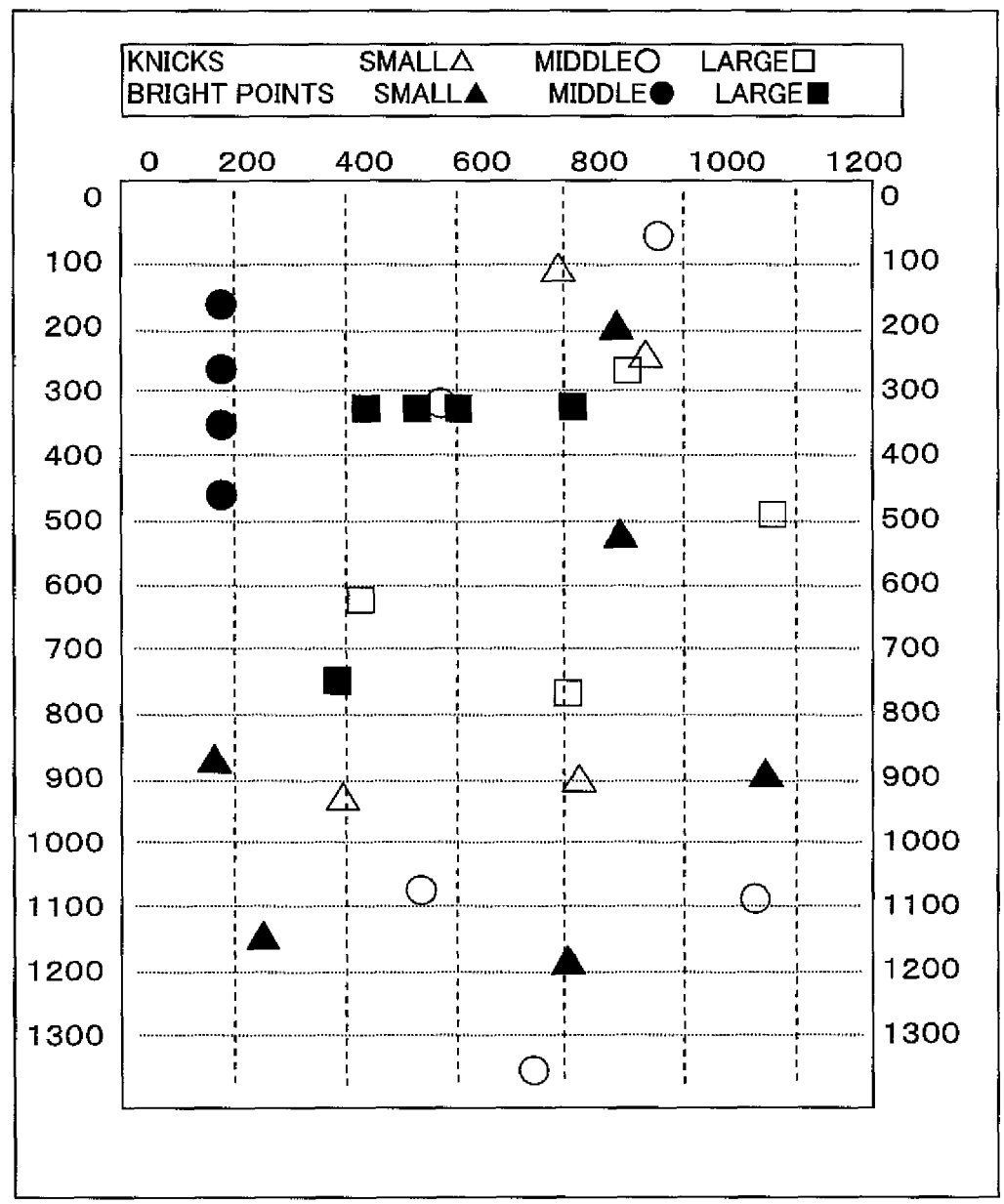
[FIG.3]

[FIG.4]

DELIVERY SCHEDULE (SCHEDULE OF ORDER INFORMATION)

| DESTINATION OF DELIVERY (DESTINATION OF SHIPPING) | PRODUCT NUMBER | STANDARD | SHIPPING SCHEDULE | NUMBER OF SHEETS |
|---|---|---|---|---|
| A Co. Ltd | AAA0001 | VA-46 | | 1200 |
| B Co. Ltd | BBB0002 | VA-46-12 | | 800 |
| C Co. Ltd | CCC0003 | VA-47 | | 800 |
| D Co. Ltd | DDD0004 | VA-48 | | 1000 |
| : | | | : | : |

CANDIDATE LOT (IDENTIFIED BY PRODUCTION LOT)

| LOT No. | NUMBER OF PRODUCTS TAKEN | YIELD | SOURCE LENGTH | REQUIRED SOURCE LENGTH | REMAINING LENGTH | N.B. |
|---|---|---|---|---|---|---|
| XXXXX-03 | | | | 1350 | | |
| XXXXX-07 | | | | 1224 | | |
| XXXXX-02 | | | | 1121 | | |
| XXXXX-08 | | | | 1559 | | |
| : | | | | : | | |

[FIG.5]

MASTER

| DEFECT ITEM NAME | DEFECT SIZE STANDARD | | STANDARD NUMBER OF DEFECTS | NUMBER OF DEFECTS | |
|---|---|---|---|---|---|
| | LOWER LIMIT | UPPER LIMIT | | WITHIN THE STANDARD | OUT OF THE STANDARD |
| KNICKS | 0.1 | 0.3 | 3 | 378 | 12 |
| BRIGHT POINTS | 0.2 | 0.5 | 2 | 20 | 0 |
| FOREIGN SUBSTANCES | 0.1 | 0.2 | 1 | 5 | 1 |

SIMULATION

| DEFECT SIZE STANDARD | | STANDARD NUMBER OF DEFECTS | NUMBER OF DEFECTS | |
|---|---|---|---|---|
| LOWER LIMIT | UPPER LIMIT | | WITHIN THE STANDARD | OUT OF THE STANDARD |
| 0.1 | 0.2 | 3 | 370 | 20 |
| 0.2 | 0.5 | 2 | 20 | 0 |
| 0.1 | 0.2 | 1 | 5 | 1 |

[FIG.6]

SIMULATION OF THE NUMBER OF PRODUCTS TAKEN

BACK    NEXT    FLOW DIRECTION SCALE  1/1    DEFECT STANDARD    CLOSE    ☐ GOOD PRODUCT

CODE PRINTING SIDE 0m                                                                                      10m

LOT No.  XXX-09

| | SOURCE LENGTH | SOURCE WIDTH | EFFECTIVE WIDTH OF THE SOURCE |
|---|---|---|---|
| | 1127 | 1552.13 | 1492.13 |

NUMBER OF DEFECTS  ...    YIELD  80.1

NUMBER OF PRODUCTS TAKEN

| PRODUCT NUMBER | STANDARD | GOOD PRODUCT | SLIT WIDTH | NUMBER OF TIMES OF SKIPPING | TOTAL NUMBER OF SKIPS | RECEIVED-ORDER NO. |
|---|---|---|---|---|---|---|
| AAAA-03 | VA-46 | 2756 | 709 | 7 | 1360 | |
| BBBB-04 | VAT32 | 3491 | 567 | 15 | 365 | |

[FIG.7]

| SET LOT No. | XXXXX-03 | | SOURCE LENGTH | 1224 | | |
|---|---|---|---|---|---|---|
| DESTINATION OF DELIVERY (DESTINATION OF SHIPPING) | PRODUCT NUMBER | | STANDARD | | SHIPPING SCHEDULE | NUMBER OF SHEETS |
| A CO. | AAA0001 | | VA-46 | | | 1200 |

CANDIDATE LOT (IDENTIFIED BY PRODUCTION LOT)

| LOT No. | NUMBER OF PRODUCTS TAKEN | | YIELD | SOURCE LENGTH | REQUIRED SOURCE LENGTH | REMAINING LENGTH | N.B. |
|---|---|---|---|---|---|---|---|
| XXXXX-03 | 1250 | +50 | 80.3 | 1350 | 1224 | 126 | |
| XXXXX-07 | 1008 | −192 | 79.8 | 1224 | 1224 | 0 | |
| XXXXX-02 | 980 | −220 | 78.3 | 1121 | 1121 | 0 | |
| XXXXX-08 | 1374 | +174 | 77.2 | 1559 | 1320 | 239 | |
| ... | | | | | | | |

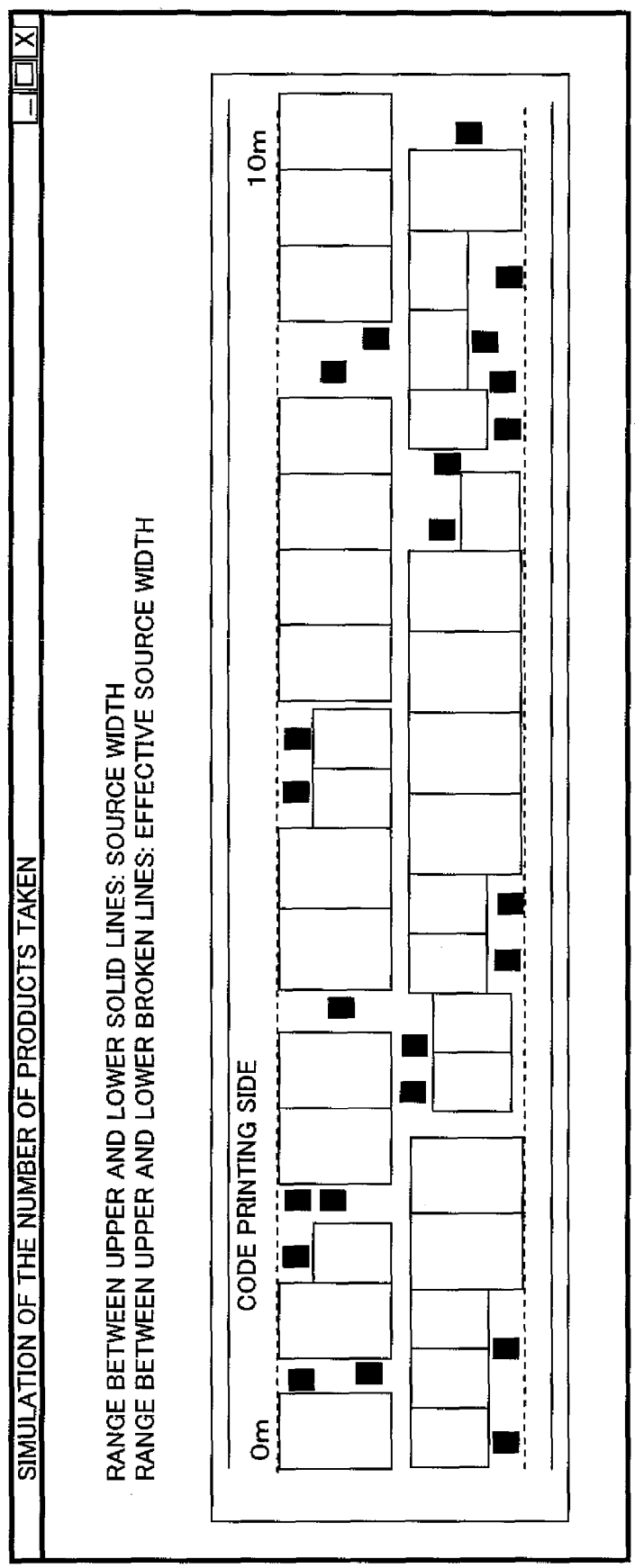

[FIG.9] SOURCE TO BE SHIPPED (SHEET-SHAPED PRODUCT SOURCE AFTER SLITTING)
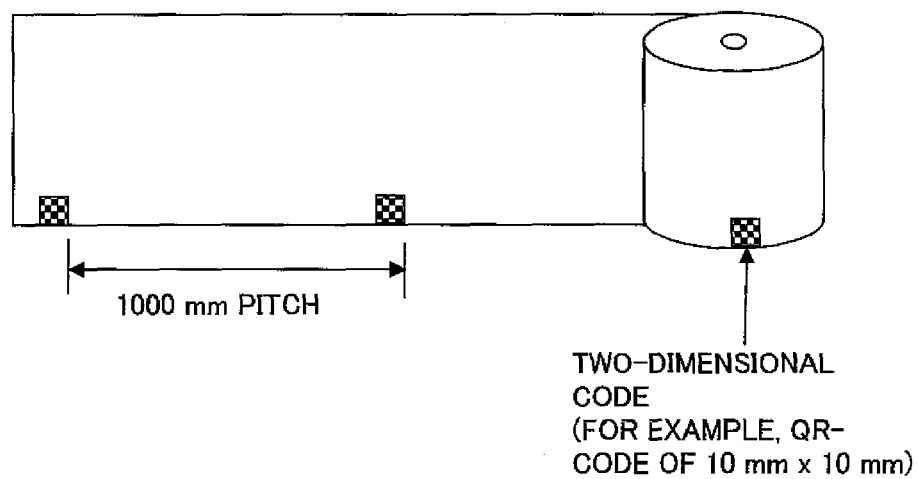

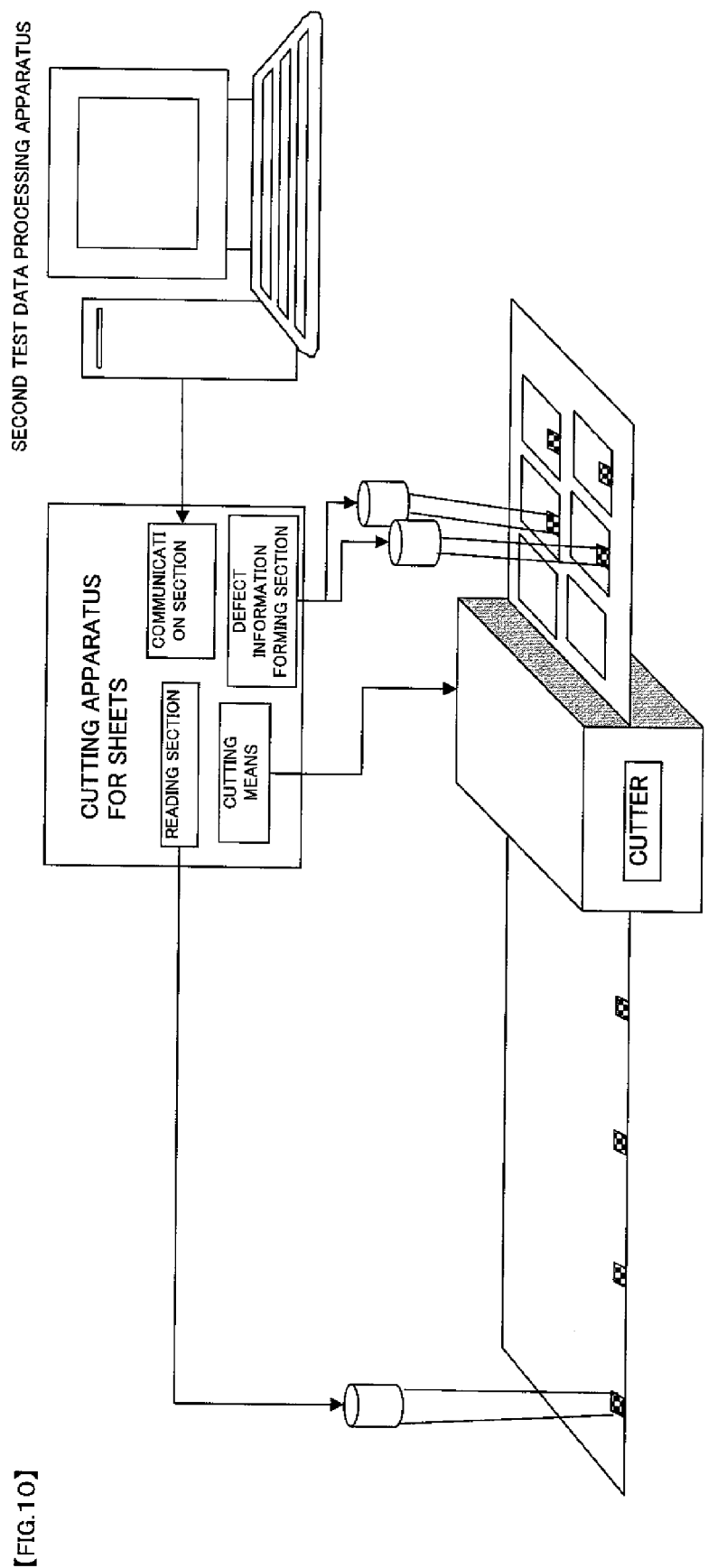
[FIG. 10]

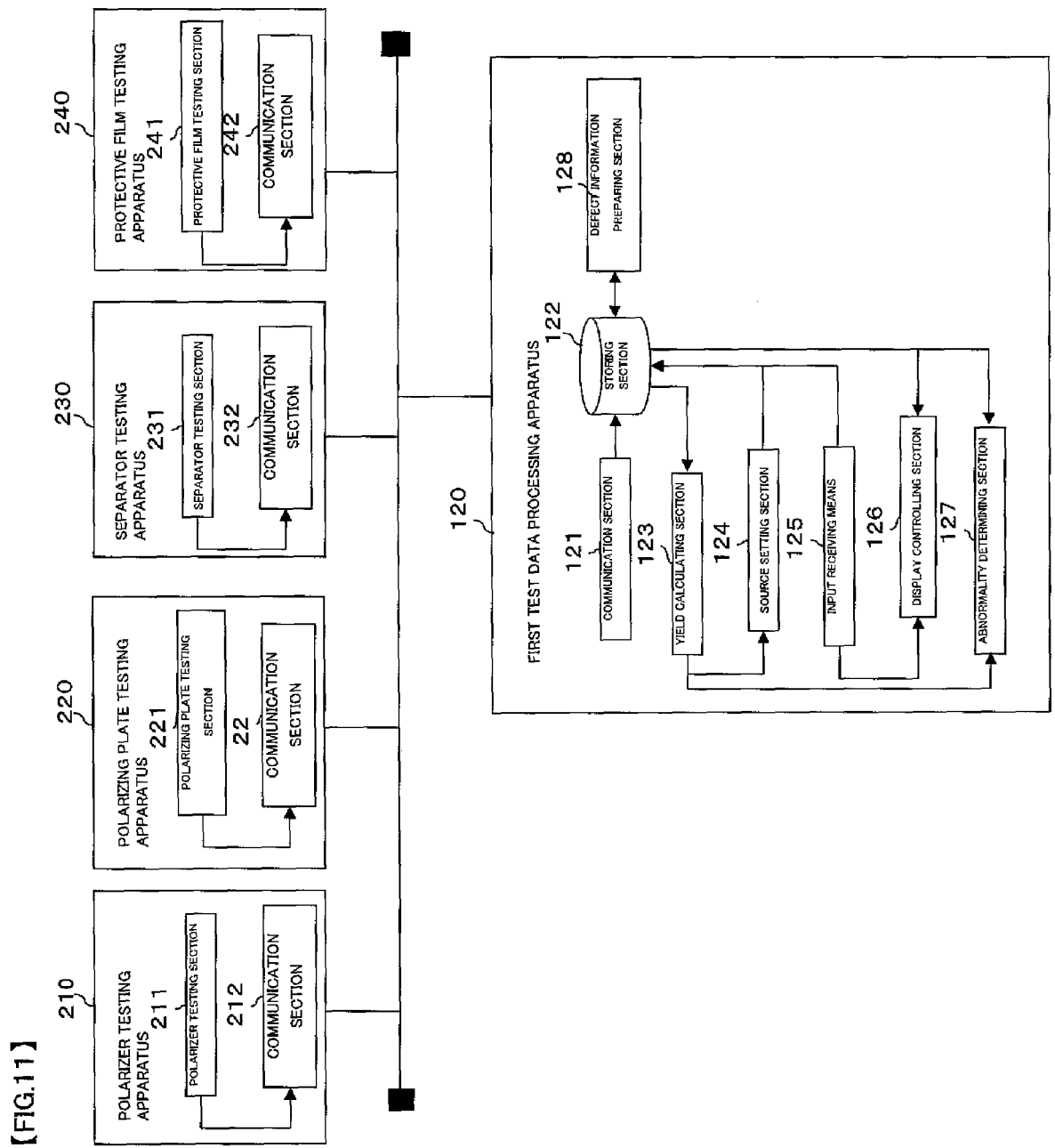

[FIG.12]
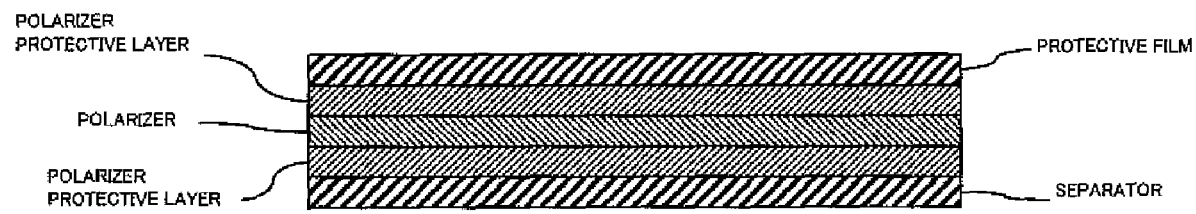

APPARATUS FOR TESTING DEFECTS OF SHEET-SHAPED PRODUCT HAVING OPTICAL FILM, APPARATUS FOR PROCESSING TEST DATA THEREOF, APPARATUS FOR CUTTING THE SAME, AND PRODUCTION THEREOF

BACKGROUND OF THE INVENTION

1. Field of the Invention

The present invention relates to an apparatus for testing defects of a sheet-shaped product having an optical film, an apparatus for processing the test data thereof, an apparatus for cutting the same, and a production system thereof. More particularly, in the event of testing the defects of a sheet-shaped product having at least an optical film which is a member of an optical displaying apparatus, the present invention relates to detecting the defects of a monolayer body and/or a laminate body constituting the sheet-shaped product in a state in which a protective layer on a surface of the sheet-shaped product is not disposed, and using the defect information for producing the sheet-shaped product provided in separate sheets.

2. Description of the Related Art

Conventionally, in a maker for producing an optical film, a band-shaped sheet-shaped product having an optical film member is produced by collecting and winding it in a roll form or on a different production line for each step. As this "band-shaped sheet-shaped product", there are, for example, a polarizing plate source, a retardation plate source, and a laminate film source of a polarizing plate and a retardation plate used in a liquid crystal display device.

An adhesive agent is used for bonding this sheet-shaped product with an optical displaying unit. This adhesive agent is formed in advance as an adhesive layer on the sheet-shaped product, and further a release film (which may also be referred to as a separator) is formed for protection of the adhesive layer.

A sheet-shaped product having a polarizing plate with a laminate structure of FIG. 12 will be shown, and a conventional example of the steps for producing this sheet-shaped product will be described below. First, as preliminary steps, there are (A) a step of obtaining a polarizer, where the polarizer is obtained by drying a polyvinyl alcohol (PVA) film subjected to a dyeing/crosslinking and stretching process, (B) a step of producing a polarizing plate, where the polarizing plate is produced by bonding a triacetylcellulose (TAC) film via an adhesive agent on both surfaces of the polarizer and laminating a polarizer protective layer; here, in the drawings, an antiglare process is performed in advance on the TAC film to be laminated thereon, (C) a step of bonding a separator and a protective film, where the separator is bonded via a strong adhesive agent on one surface of the polarizing plate (lower side in the drawings) and the protective film is bonded via a weak adhesive agent on the other surface (upper side in the drawings). Here, the strong adhesive agent is applied in advance on the separator, and the weak adhesive agent is applied in advance on the protective film. The strong adhesive agent applied on the separator is transferred to the TAC after releasing the separator. The weak adhesive agent applied on the protective film remains as it is formed on the protective film after releasing the protective film, so that substantially the weak adhesive agent is not transferred to the TAC. Through the above-described preliminary steps, a band-shaped sheet-shaped product is produced, collected and wound in a roll form, and subjected to subsequent processes.

In these preliminary steps (A, B, C), a predetermined test is carried out for each step by a testing person. For example, in the case of the step (A), during the transportation of the PVA source, the testing person confirms the defects (foreign substances, stain, twist, surface-adhering substances, and the like) by eye inspection at the timings of the start and the end of winding of the roll. Also, in the case of the step (B), in collecting and winding the obtained polarizing plate source in a roll form, the testing person confirms the defects (foreign substances, stains, knicks, twists, creases, and the like) by eye inspection. Also, the polarizing plate source after bonding is automatically tested by a defect testing apparatus (a known apparatus for capturing images of foreign substances, stain, and the like with a camera, and determining the defects by image processing); the defects are confirmed by a monitor; and the test was mainly used for state management (supervision) by monitoring the defects.

Also, in the case of the step (C), in collecting and winding the obtained band-shaped sheet-shaped product source in a roll form, the testing person confirms the defects (foreign substances, stain, twist, surface-adhering substances, and the like) by eye inspection at the timings of the start and the end of winding of the roll, and performed the ranking (good, bad, permissibility of shipping) of the sheet-shaped product source by evaluating these defects.

Subsequently, as the posterior steps, there is (D) a step of testing the source roll. Here, the appearance of the sheet-shaped product roll is tested by a roll-form automatic source testing apparatus and/or by eye inspection of a testing person. The roll-form automatic source testing apparatus is a known apparatus that captures images of poor winding, poor appearance, and the like with a camera, and performs image processing to determine the defects. Also, there is (E) a step of cutting into a sheet-shaped product provided in separate sheets. Here, a sheet-shaped product is drawn out from the source roll, and is cut to have a predetermined size. As the cutting method, there are, for example, constant-measure cutting, continuous punching-out, and the like. Also, there is (F) a step of testing the sheet-shaped product provided in separate sheets. Here, testing by a sheet-form automatic testing apparatus and by eye inspection of a testing person are carried out. The sheet-form automatic testing apparatus is an apparatus that automatically tests the defects of the sheet-shaped product provided in separate sheets, where light is radiated; images of the reflected light thereof or images of transmitted light thereof are captured with an imaging section such as a line sensor or a two-dimensional TV camera; and the defects are detected on the basis of the captured image data. Also, the image data are captured in a state in which a polarizing filter for testing intervenes in the optical path between the light source and the imaging section. Typically, the polarization axis (for example, the polarization absorption axis) of this polarizing filter for testing is disposed to be in a state (crossed nicol form) perpendicular to the polarization axis (for example, the polarization absorption axis) of the polarizing plate which is an object of testing. By disposing it in crossed nicol, an image of total black is input from the imaging section if there are no defects; however, when there are defects, that part will not be black and will be detected as bright points. Therefore, the defects can be detected by setting a suitable threshold value.

As described above, in the posterior steps (D, E, F), the sheet-shaped product source wound in a roll form is drawn out and is cut into a sheet-shaped product provided in separate sheets of a predetermined size, followed by a predetermined defect testing to determine the quality for shipping.

In the above-described whole production steps, the defect testing of individual sheet-shaped products are carried out after being cut into a sheet-shaped product provided in separate sheets. Therefore, the product is determined to have a poor quality, for example, if one defect is present in the sheet-shaped product, thereby raising a problem in that the yield of the final sheet-shaped product provided in separate sheets obtained from the source roll will be poor.

Also, in the case of testing a sheet-shaped product provided in separate sheets, the product is in a state in which a separator or a protective film is bonded on the sheet surface. When the sheet-shaped product provided in separate sheets is tested in this state, because the separator and the protective film have a birefringence property (retardation), the linearly polarized light will be elliptically polarized light in such a case, so that substantially the polarizing plate and the polarization filter for testing will not be in a state of crossed nicol. As a result, this raises a problem in that the testing of the defects of the polarizing plate included in the sheet-shaped product cannot be performed with a good precision.

Here, as an apparatus for testing defects of a laminate film that solves the aforementioned problem, a polarizing plate testing apparatus disclosed in Japanese Patent Application Laid-Open (JP-A) No. 2005-9919 is known in the art. This polarizing plate testing apparatus includes a light source and a polarization filter for testing that converts the light from this light source into linearly polarized light, where this linearly polarized light is input into a polarizing plate having a protective film (corresponding to a retardation layer), and the defects are detected on the basis of transmitted light images thereof. Further, on the optical path on which the light from the light source is transmitted through the polarizing plate having a protective film, a retardation plate that compensates for the birefringence of the light caused by the protective film is disposed. By separately disposing this retardation plate, the phase change caused by the protective film is cancelled, so as to compensate for the birefringence of the light caused by the protective film. Further, in order to compensate for the birefringence caused by the protective film that differs slightly product by product, there is disclosed a construction example in which an optical element for variable polarized light that can adjust the phase angle of light with use of voltage is disposed.

However, in the above-described JP-A No. 2005-9919, there is a need to dispose the retardation plate for testing or the optical element for variable polarized light separately, leading to additional increase in the number of components and also inviting decrease in the quantity of light of the light source due to the presence of additional intervening components. This lowers the precision of testing, so that there may be cases that cannot withstand the demand for testing of high precision and high product quality that are required in the polarizing plates of recent years.

Also, in order to increase the precision of testing the defects, testing by eye inspection of a person is carried out; however, since this is an eye inspection, it is necessary to take a long period of time for the testing. For this reason, the productivity is poor and a large number of testing persons are needed, thereby raising a problem of leading to increase in the production costs.

Further, in the testing after being cut into separate sheets, determination of being good or bad is carried out using a uniform threshold value (the severest value) as a condition. However, depending on the user (for example, a liquid crystal apparatus assembling manufacturer), the determination of being good or bad of the degree of the defects may differ. There is a case such that, even if one product is bad for a certain manufacturer, the product may have an excessive quality for another manufacturer. Then, there is a demand from the manufacturer side for carrying out testing that meets the quality requirement of each manufacturer and for cost reduction and shortening of the deadline of receiving the products. Due to such demands, an improvement in the testing steps has been strongly desired.

The present invention has been made in view of the above-described circumstances, and an object thereof is to provide a defect testing apparatus for testing the defects of a sheet-shaped product having at least an optical film which is a member of an optical displaying apparatus that can improve the yield, reduce the production costs, and greatly improve the productivity by using a determination condition that differs user by user, as well as a test data processing apparatus thereof, a cutting apparatus thereof, a production system thereof, and a test data processing method.

SUMMARY OF THE INVENTION

In order to solve the above-described problems, the inventors of the present invention have repeatedly made eager studies, thereby completing the following invention.

A defect testing apparatus according to the present invention is a defect testing apparatus for testing defects of a sheet-shaped product having at least an optical film which is a member of an optical displaying apparatus, including:

defect detecting means for detecting defects of a monolayer body and/or a laminate body constituting the sheet-shaped product in a state in which a protective layer on a surface of the sheet-shaped product is not disposed; and defect information preparing means for preparing defect information which is information related to the defects detected by said defect detecting means, wherein said defect information is used for producing the sheet-shaped product provided in a roll form or in separate sheets.

The functional effects of the above-described construction are as follows. The defect testing apparatus includes defect testing means and defect information preparing means. The "defects" are defects that are not preferable as a product, and examples thereof include foreign substances on the surface or in the inside, stains, scars, special defects (which may be referred to as knicks) that are in a form of twisted wounds that have bitten foreign substances, air bubbles, and the like. The defect detecting means can detect various defects. Further, the defect detecting means detects the defects of the monolayer body and/or the laminate body in a state in which a protective layer (for example, a separator or a protective film) on a surface of the sheet-shaped product is not disposed. Therefore, the defects can be detected with a good precision without receiving an influence of the protective layer. The defect information preparing means prepares individual defect information on the basis of the information of the defects that have been detected by each testing means. Also, the defect information preparing means can integrate the information of the defects that have been detected by each testing means, so as to prepare final defect information.

Herein, the "defect information" includes, for example, information such as information related to the kind of the defects, information related to the coordinates of the defects, the production identification information, the testing object identification information, and the like. This defect information is used for producing (for example, cutting) the sheet-shaped product provided in separate sheets. This improves the yield because the sheet-shaped product provided in a roll form or in separate sheets can be cut in accordance with the defect information. Also, there is no need to carry out the defect testing on the cut sheet-shaped product provided in separate sheets, so that the number of testing persons can be greatly reduced, thereby providing a large merit in terms of costs.

Also, in the present invention, in each testing step, the defect information can be formed on the object of testing. The formed defect information can be read in the testing of the subsequent step, integrated with the test results of the step, and further formed on the object of testing as an integrated defect information. For example, the defect information formed on the polarizing plate and the defect information formed on the separator and the protective film can be read before bonding, and the integrated defect information can be formed on the protective film after bonding.

Also, a test data processing apparatus according to the present invention includes:

defect information obtaining means for obtaining the defect information prepared in the above-described defect testing apparatus of the present invention;

yield calculating means for analyzing the defect information obtained in the defect information obtaining means and calculating a yield of the sheet-shaped product provided in a roll form or in separate sheets obtained by slitting or cutting a sheet-shaped product source according to a determination condition which is a condition for determining whether the product is good or bad; and setting means for setting a sheet-shaped product source in which the yield is above or equal to a predetermined value.

The functional effects of this construction are as follows. The defect information obtaining means obtains the defect information prepared in the defect testing apparatus. The "obtaining" is not particularly limited, so that examples are obtaining methods such as a direct key input method, a (wireless or wired) communication method, and a printed character reading.

The obtained defect information is analyzed by the yield calculating means, which then calculates the yield of the sheet-shaped product provided in a roll form or in separate sheets obtained by slitting or cutting a sheet-shaped product source according to a determination condition which is a condition for determining whether the product is good or bad. The "determination condition" is set, for example, on the basis of the number of defects per one sheet of the product and the size of the defects. Also, the determination condition includes, for example, the size of the sheets and the number of needed sheets (the number of sheets to be shipped).

In the present invention, the "yield" is obtained by dividing the total area of the good sheet-shaped product provided in separate sheets obtained from the source with the total area (or effective area) of the source. Alternatively, the "yield" is obtained by dividing the number of the good sheet-shaped products provided in separate sheets obtained from the source with the theoretical maximum number of the products to be obtained from the source. Also, the yield value is preferably represented in percentage.

Then, a sheet-shaped product source in which the yield is above or equal to a predetermined value is set by the setting means. For example, in the case in which one wishes to set an optimum sheet-shaped product source from a plurality of sheet-shaped product sources, the sheet-shaped product source is set, for example, if the yield is above or equal to a predetermined value. As the predetermined value, the maximum yield value can be set among the plurality of sheet-shaped product sources. If there are data of the destination of shipping (destination of transportation) tied with a string in the determination condition, the sheet-shaped product source roll that has been set here will be shipped to that destination of shipping (destination of transportation).

Therefore, since the defects of the sheet-shaped product source roll are known in advance, a sheet-shaped product source roll having an optimum yield, for example, can be set in accordance with the determination condition.

Also, a cutting apparatus according to the present invention includes:

obtaining means for obtaining slit width and defect information of the sheet-shaped product source that has been set in the above-described defect information test data processing apparatus of the present invention;

cutting means for cutting the sheet-shaped product source with the slit width obtained by the obtaining means; and defect information forming means for forming the obtained defect information on the protective layer of the sheet-shaped product source that has been cut with the slit width.

The functional effects of this construction are as follows. The cutting apparatus is used for cutting the sheet-shaped product source roll produced in the previous steps thereof into a slit width. The obtaining means obtains the slit width of the sheet-shaped product source that has been set in the defect information test data processing apparatus and the defect information of the source. The cutting means slits the set sheet-shaped product source roll with this slit width. Depending on the slit, one source roll or two or more source rolls may be formed from one source roll. Then, the defect information forming means forms the obtained defect information on the protective layer of the sheet-shaped product source that has been slit. The forming method is not particularly limited, and examples thereof are printing, baking, and the like. This defect information will be used for production (cutting) of the sheet-shaped product provided in separate sheets.

A production system for producing a sheet-shaped product source according to the present invention is a production system for producing a sheet-shaped product source including an optical film for producing a sheet-shaped product source having at least an optical film which is a member of an optical displaying apparatus, including:

defect detecting means for detecting defects of a monolayer body and/or a laminate body constituting the sheet-shaped product in a state in which a protective layer on a surface of the sheet-shaped product is not disposed;

defect information preparing means for preparing defect information which is information related to the defects detected by the defect detecting means;

yield calculating means for analyzing the defect information prepared in the defect information preparing means and calculating a yield of the sheet-shaped product provided in a roll form or in separate sheets obtained by slitting or cutting a sheet-shaped product source according to a determination condition which is a condition for determining whether the product is good or bad;

setting means for setting a sheet-shaped product source in which the yield is above or equal to a predetermined value;

cutting means for cutting the set sheet-shaped product source with a slit width; and defect information forming means for forming defect information on the protective layer of the cut sheet-shaped product source.

This production system for producing a sheet-shaped product source including an optical film includes means of the defect testing apparatus, the test data processing apparatus, and the cutting apparatus that have been already described, and the functional effects thereof are also as described above.

A cutting apparatus for obtaining a sheet-shaped product provided in separate sheets from a sheet-shaped product source according to the present invention includes:

defect information reading means for reading the defect information formed on the sheet-shaped product source that has been cut to have a predetermined slit width or that has not been subjected to slit cutting in the cutting apparatus or in the production system described above; and cutting means for analyzing the defect information that has been read by the defect information reading means, calculating a cutting position according to a determination condition which is a condition for determining whether the product is good or bad, and producing a sheet-shaped product provided in separate sheets by cutting the sheet-shaped product source.

The functional effects of this construction are as follows. This cutting apparatus includes defect information reading means for reading the defect information formed on the sheet-shaped product source that has been cut to have a predetermined slit width or that has not been subjected to slit cutting. Then, the cutting means analyzes the defect information that has been read, calculates a cutting position according to a determination condition which is a condition for determining whether the product is good or bad, and produces a sheet-shaped product provided in separate sheets by cutting the sheet-shaped product source.

According to the cutting means, the source can be cut on the basis of the defect information, so that it will be suitable and the yield will be optimal (or will be above or equal to a predetermined value).

Also, the cutting apparatus of the present invention preferably further includes product information forming means for forming product information corresponding to the sheet-shaped product on the cut sheet-shaped product.

The "product information" is information for identifying the sheet-shaped product provided in separate sheets and includes, for example, the production identification number, and the defect information. Since the product information is formed on individual sheet-shaped products provided in separate sheets, the collecting work (loading while determining whether the products have defects or are good products) can be automated. Also, the automatic counting of the number of sheets after cutting can be carried out, so that where and what products have been completed can be definitely controlled. Also, the work of counting, the posterior processing steps, and the management of the number of the products to be shipped, which have been carried out by persons, can be automated. Also, the frequency of use and the cutting quality of the devices such as the cutting blade can be managed. Also, the state of operation of the equipment can be definitely controlled. Also, the product information includes the production identification number, thereby the tracing investigation can be simply and easily performed.

A production system for producing a sheet-shaped product including an optical film according to the present invention is a production system for producing a sheet-shaped product including an optical film for producing a sheet-shaped product having at least an optical film which is a member of an optical displaying apparatus, including:

defect detecting means for detecting defects of a monolayer body and/or a laminate body constituting the sheet-shaped product in a state in which a protective layer on a surface of the sheet-shaped product is not disposed;

defect information preparing means for preparing defect information which is information related to the defects detected by the defect detecting means;

yield calculating means for analyzing the defect information prepared in the defect information preparing means and calculating a yield of the sheet-shaped product provided in separate sheets obtained by cutting the sheet-shaped product source according to a determination condition which is a condition for determining whether the product is good or bad;

setting means for setting a sheet-shaped product source in which the yield is above or equal to a predetermined value;

first cutting means for cutting the set sheet-shaped product source with a slit width;

defect information forming means for forming defect information on the protective layer of the cut sheet-shaped product source;

defect information reading means for reading the defect information formed by the defect information forming means; and second cutting means for analyzing the defect information that has been read by the defect information reading means, and producing a sheet-shaped product provided in separate sheets by cutting the sheet-shaped product source according to a determination condition which is a condition for determining whether the product is good or bad.

Also, the production system of the present invention preferably further includes defect information forming means for forming defect information corresponding to the sheet-shaped product on the cut sheet-shaped product provided in separate sheets.

This production system has the functions of the defect testing apparatus, the test data processing apparatus, the cutting apparatus for slitting, and the cutting apparatus for obtaining the sheet-shaped product provided in separate sheets from the sheet-shaped product source that have been already described above.

A test data processing apparatus according to the present invention includes:

defect information obtaining means for obtaining defect information related to defects obtained by testing a monolayer body and/or a laminate body constituting a sheet-shaped product having at least an optical film which is a member of an optical displaying apparatus in a state in which a protective layer on a surface of the sheet-shaped product is not disposed; and cutting position information calculating means for analyzing the defect information obtained in the defect information obtaining means and calculating cutting position information of the sheet-shaped product source according to a determination condition which is a condition for determining whether the product is good or bad.

The test data processing apparatus having this construction obtains defect information related to defects obtained by testing a monolayer body and/or a laminate body constituting a sheet-shaped product having at least an optical film which is a member of an optical displaying apparatus in a state in which a protective layer on a surface of the sheet-shaped product is not disposed. Then, the test data processing apparatus can analyze the defect information and calculate the cutting position information of the sheet-shaped product source according to a determination condition which is a condition for determining whether the product is good or bad.

Also, another cutting apparatus according to the present invention includes:

cutting position information obtaining means for obtaining the cutting position information that has been calculated in the test data processing apparatus described above;

defect information reading means for reading the defect information of the sheet-shaped product source formed on the sheet-shaped product source that has been cut to have a predetermined slit width or that has not been subjected to slit cutting; and cutting means for analyzing the defect information that has been read by the defect information reading means, and calculating the cutting position and producing a sheet-shaped product provided in separate sheets by cutting the sheet-shaped product source in accordance with the cutting position information obtained by the cutting position information obtaining means.

With this construction, the defect information can be analyzed by the test data processing apparatus, and the sheet-shaped product source can be cut on the basis of the calculated cutting position information, whereby a sheet-shaped product provided in separate sheets can be suitably produced.

Also, the cutting apparatus of the present invention preferably further includes product information forming means for forming product information corresponding to the sheet-shaped product on the cut sheet-shaped product provided in separate sheets.

The functional effects of this construction are as described above.

Also, another test data processing apparatus of the present invention includes:

input receiving means for receiving input of a determination condition which is a condition for determining whether a product is good or bad;

defect information obtaining means for obtaining defect information related to defects obtained by testing a monolayer body and/or a laminate body constituting a sheet-shaped product having at least an optical film which is a member of an optical displaying apparatus in a state in which a protective layer on a surface of the sheet-shaped product is not disposed;

yield calculating means for analyzing the defect information and calculating a yield according to the determination condition; and display controlling means for controlling so as to allow displaying means to display the calculated yield.

With this construction, the defect information can be analyzed; a yield can be calculated in accordance with the input determination condition; and this yield can be displayed by the displaying means. Therefore, the yield can be calculated in advance by using the defect information and the determination condition before performing the slit processing or the sheet-cut processing on the sheet-shaped product source, thereby largely contributing to improvement in the productivity.

Also, in the test data processing apparatus of the present invention, in the case where the yield is calculated, it is preferable to calculate by adopting a skip-cut method. With this construction, the skip cut can be performed, thereby leading to an improvement in the yield. The skip cut method as referred to herein means a method of cutting the source while avoiding only the defect part that is determined to be a bad part on the basis of the defect information.

Also, in the test data processing apparatus of the present invention, the display controlling means preferably develops a sheet-shaped product source and controls so as to display the sheet-shaped product provided in separate sheets obtained as a good product so as to overlap with the developed sheet-shaped product source. With this construction, the sheets provided as separate sheets can be displayed to overlap with the developed source, so that the number of sheets to be taken and the taking position state can be easily confirmed. Also, the apparatus is preferably constructed so that the defect information is also displayed. By displaying together with the defect information, the kind and the coordinates of the defects can also be confirmed.

Also, another test data processing method according to the present invention includes the steps of:

receiving input of a determination condition which is a condition for determining whether a product is good or bad;

obtaining defect information related to defects obtained by testing a monolayer body and/or a laminate body constituting a sheet-shaped product having at least an optical film which is a member of an optical displaying apparatus in a state in which a protective layer on a surface of the sheet-shaped product is not disposed;

analyzing the defect information and calculating a yield according to the determination condition; and allowing displaying means to display the calculated yield.

The functional effects of this construction have the functional effects of the test data processing apparatus described above; however, specific means thereof is not limited to this alone.

BRIEF DESCRIPTION OF THE DRAWINGS

FIG. 1 is a view showing a functional block of a production system;

FIG. 2 is a view showing one example of a production step and a testing step;

FIG. 3 is a view showing one example of information of displayed defects;

FIG. 4 is a view describing data processing in a test data processing apparatus;

FIG. 5 is a view describing data processing in a test data processing apparatus;

FIG. 6 is a view describing data processing in a test data processing apparatus;

FIG. 7 is a view describing data processing in a test data processing apparatus;

FIG. 8 is a view describing data processing in a test data processing apparatus;

FIG. 9 is a view describing a source roll on which defect information is formed;

FIG. 10 is a view describing a process of forming product information;

FIG. 11 is a view showing a functional block of a production system; and

FIG. 12 is a view describing a construction of a sheet-shaped product having a polarizing plate.

DETAILED DESCRIPTION OF THE PREFERRED EMBODIMENTS

Hereafter, preferable embodiments of the present invention will be described.

<Sheet-Shaped Product>

As an example of the sheet-shaped product dealt with in the present invention, a polarizing plate source will be described. The polarizing plate source is formed in a long band shape, and polarizing plates having individual sizes can be obtained by punching out (or cutting) from the polarizing plate source in a film form. The polarizing plate source can be obtained by bonding, for example, a triacetylcellulose film (transparent polarizer protective layer) on both of the front and rear surfaces of a polyvinyl-alcohol-based film (polarizer) that has been produced in advance. It is necessary to detect the defects (scars, foreign substances, knicks, stains, and the like) that are present on the surface or in the inside of the polarizing plate source made to have a multiple layer structure. These can be detected by detecting means described later.

As described also in the prior art section, the polarizing plate source is produced by a production method including (A) a step of obtaining a polarizer, (B) a step of producing a polarizing plate, and (C) a step of bonding a separator and a protective film.

The processes of dyeing, crosslinking, and stretching the polyvinyl-alcohol-based film need not be carried out separately, but may be carried out simultaneously. Also, the order of the processes may be arbitrary. Herein, as the polyvinyl-alcohol-based film, a polyvinyl-alcohol-based film subjected to a swelling process may be used. Generally, a polyvinyl-alcohol-based film is immersed into a solution containing iodine or a dichroic dye so as to let the iodine or the dichroic dye be adsorbed for dyeing and, after being washed, subjected to monoaxial stretching in a solution containing boric acid, borax, or the like in a stretching magnification of 3 times to 7 times, followed by drying. By drying after being stretched in a solution containing iodine or a dichroic dye and after being further stretched (two-step stretching) in a solution containing boric acid, borax, or the like, the orientation of iodine will be high, and the polarization degree characteristics will be good, so that it is especially preferable.

Examples of the above-described polyvinyl-alcohol-based polymer are those obtained by polymerizing vinyl acetate and then performing saponization, those obtained by copolymerizing a small amount of polymerizable polymers such as unsaturated carboxylic acid, unsaturated sulfonic acid, and cationic monomers with vinyl acetate, and the like. The average polymerization degree of the polyvinyl-alcohol-based polymer is not particularly limited, so that those having an arbitrary polymerization degree can be used; however, the polymerization degree is preferable 1000 or higher, more preferably 2000 to 5000. Also, the saponization degree of the polyvinyl-alcohol-based polymer is preferably 85 mol % or higher, more preferably 98 to 100 mol %.

The thickness of the polarizer to be produced is typically 5 to 80 μm; however, it is not limited to this alone. Also, the method of adjusting the thickness of the polarizer is not particularly limited, so that ordinary methods such as tenter, roll stretching, and press-rolling can be used.

The process of bonding the polarizer and a transparent polarizer-protective layer constituting the protective layer is not particularly limited, so that it can be carried out, for example, via an adhesive made of a polyvinyl-alcohol-based polymer, an adhesive made of at least a water-soluble crosslinking agent of the polyvinyl-alcohol-based polymer such as boric acid, borax, glutaraldehyde, melamine, or oxalic acid. Such an adhesive layer is formed as a layer obtained by applying and drying an aqueous solution; however, in preparing the aqueous solution, other additives and catalysts such as acid can be blended in accordance with the needs.

As the polarizer protective layer disposed on one side or on both sides of the polarizer, a suitable transparent film can be used. Among these, a film made of a polymer being excellent in transparency, mechanical strength, thermal stability, water-shielding property, and the like is preferably used. Examples of the polymer are acetate-based resin such as triacetylcellulose, polycarbonate-based resin, polyester-based resin such as polyallylate or polyethylene terephthalate, polyimide-based resin, polysulfone-based resin, polyethersulfone-based resin, polystyrene-based resin, polyolefin-based resin such as polyethylene or polypropylene, polyvinylalcohol-based resin, polyvinyl-chloride-based resin, polynorbornene-based resin, polymethyl-methacrylate-based resin, liquid crystal polymer, and the like. The film may be produced by any of the casting method, the calendaring method, and the extrusion method.

Also, another example of the film is a polymer film disclosed in Japanese Patent Application Laid-Open (JP-A) No. 2001-343529 (WO01/37007), for example, a resin composition containing (A) a thermoplastic resin having a substituted and/or non-substituted imide group in a side chain and (B) a thermoplastic resin having substituted and/or non-substituted phenyl and nitrile groups in a side chain. A specific example is a film made of a resin composition containing an alternate copolymer of isobutyrene and N-methylmaleimide and an acrylonitrile/styrene copolymer. As the film, a film made of a mixed and extruded product of the resin composition can be used. Since these films have only a small retardation and a small optical elastic modulus, inconveniences such as unevenness caused by the distortion of the polarizing plate can be eliminated. Also, since the humidity transmitting degree is small, the film is excellent in the durability against addition of moisture.

Also, the polarizer protective layer is preferably colored as little as possible. Therefore, a protective film in which the retardation value in the film thickness direction represented by $Rth=[(nx+ny)/2-nz]\cdot d$ (where nx and ny are principal refractive indices within the film plane; nz is a refractive index in a film thickness direction; and d is the film thickness) is −90 nm to +75 nm is preferably used. By using such a film in which the retardation value (Rth) in the thickness direction is −90 nm to +75 nm, the coloring (optical coloring) of the polarizing plate caused by the protective film can be almost completely eliminated. The retardation value (Rth) in the thickness direction is more preferably −80 nm to +60 nm, most preferably −70 nm to +45 nm.

In view of the polarization characteristics, the durability, and the like, an acetate-based resin such as triacetylcellulose is preferable, and in particular a triacetylcellulose film whose surface has been subjected to saponization process with an alkali is preferable.

The thickness of the polarizer protective layer is arbitrary; however, typically the thickness is 500 μm or below, preferably 1 to 300 μm, more preferably 5 to 200 μm, for the purpose of thickness reduction of the polarizing plate. Here, in the event that the polarizer protective layer made of a transparent film is disposed on both surfaces of the polarizing film, transparent films made of different polymers or the like may be used on the front and rear surfaces.

The polarizer protective layer may be subjected to a hard-coating process, an antireflection process, processes performed for the purposes of preventing or diffusing sticking, or antiglaring. The hard-coating process is carried out for the purpose of preventing scars to be formed on the polarizing plate surface, and the hard-coating can be formed by adding a cured skin film being excellent in hardness or slipping property made by an ultraviolet-curing resin such as a silicone-based one onto the surface of the transparent protective film.

On the other hand, the antireflection process is carried out for the purpose of preventing reflection of external light on the polarizing plate surface, and can be achieved by forming an antireflection film according to the prior art. Also, the sticking preventing process is performed for the purpose of preventing close adhesion to adjacent layers, and the antiglaring process is carried out for the purpose of preventing hindrance of the visibility of the light transmitted through the polarizing plate caused by reflection of external light on the surface of the polarizing plate, and can be formed, for example, by imparting a fine undulation structure on the surface of the transparent protective film by a suitable method such as the surface roughening treatment by the sandblast method or the emboss processing method, or the method of blending transparent fine particles.

The above-described transparent fine particles may be, for example, silica, alumina, titanium, zirconia, tin oxide, indium oxide, cadmium oxide, antimony oxide, or the like having an average particle size of 0.5 to 20 μm. Inorganic fine particles having an electric conductivity may be used, and organic fine particles made of crosslinked or non-crosslinked polymer particulate substances may be used. The amount of using the transparent fine particles is typically 2 to 70 parts by mass, preferably 5 to 50 parts by mass, relative to 100 parts by mass of the transparent resin.

Further, the antiglaring layer blended with the transparent fine particles can be provided as the transparent protective layer itself or as a layer applied onto the surface of the transparent protective layer. The antiglaring layer may also serve as a diffusing layer for enlarging the viewing angle (viewing angle compensating function) by diffusing the light transmitted through the polarizing plate. Here, the antireflection layer, the sticking preventing layer, the diffusing layer, the antiglaring layer, and the like described above may be provided separately from the transparent protective layer as optical layers made of sheets on which those layers are disposed.

In practical use, the sheet-shaped product according to the present invention can be used as an optical film by laminating various optical layers. The optical layers are not particularly limited; however, an example is a method of performing a hard-coating process, an antireflection process, surface treatments performed for the purposes of preventing sticking, diffusing, or antiglaring, or laminating a oriented liquid crystal layer for the purpose of viewing angle compensation or the like. Also, examples of the optical layer are those obtained by bonding one layer or two or more layers of an optical film used for forming a liquid crystal display device such as a reflection plate, a semitransparent plate, a retardation plate (including a wavelength plate (plate) such as ½ or ¼), or a viewing angle compensating film. In particular, when the sheet-shaped product is a polarizing plate, it can be preferably applied as a reflection-type polarizing plate or a semi-transmitting type polarizing plate made by lamination of a reflecting plate or a semitransmitting plate, an elliptic or circular polarizing plate made by lamination of a retardation plate, a wide viewing angle plate made by lamination of a viewing angle compensating layer or a viewing angle compensating film, or a polarizing plate made by lamination of a brightness-improving film.

The reflection type polarizing plate is one in which a reflection layer is provided in a polarizing plate, and is used for forming a liquid crystal display device of a type that displays by reflecting incident light coming from the visible side (display side), and has advantages such as facilitated thickness reduction of the liquid crystal display device because incorporation of a light source such as back light can be omitted. The reflection-type polarizing plate can be formed, for example, by a suitable method such as additionally disposing a reflection layer made of metal or the like on one surface of a polarizing plate via a transparent protective layer in accordance with the needs.

A specific example of a reflection-type polarizing plate is a plate in which a reflection layer is formed by additionally disposing a foil or a vapor-deposited film made of a reflective metal such as aluminum on one surface of a transparent protective film subjected to a matting process in accordance with the needs. Also, another example is a plate having a surface fine undulating structure obtained by allowing fine particles to be contained in the above-described transparent protective film and further having a reflection layer of fine undulating structure thereon. The above-described reflection layer of fine undulating structure has advantages of preventing directivity or glittering appearance by diffusing the incident light by random reflection and restraining unevenness of brightness and darkness. Also, the transparent protective film containing fine particles has advantages of further restraining the unevenness of brightness and darkness because the incident light and the reflected light thereof are diffused when passing through the film. The reflection layer having a fine undulating structure on which the surface fine undulating structure of the transparent protective film is reflected can be formed, for example, by directly adding metal to the surface of the transparent protective layer by a suitable method such as a vapor deposition method such as the vacuum vapor deposition method, ion plating method, or the sputtering method, or the plating method.

The reflection plate can also be used as a reflection sheet in which a reflection layer is disposed on a suitable film that accords to the transparent film in place of directly imparting to the transparent film (polarizer protective film) of the above-described polarizing plate. Herein, since the reflection layer is typically made of metal, the usage mode in a state in which the reflection surface thereof is covered with a transparent film or a polarizing plate is preferable in view of preventing decrease in the reflectivity caused by oxidation, and further the long-term durability of the initial reflectivity, and the avoidance of separately disposing a protective layer.

Herein, the semitransmitting polarizing plate can be obtained by making a reflection layer of semitransmittance type such as a half mirror that reflects and transmits light at the reflection layer in the above construction. The semitransmittance type polarizing plate is typically disposed on the back surface of a liquid crystal cell, and can form a liquid crystal display device or the like of a type such that, in the event that a liquid crystal display device or the like is used in a comparatively bright atmosphere, images are displayed by reflecting the incident light coming from the visible side (display side) and, in a comparatively dark atmosphere, images are displayed by using an incorporated light source such as a back light unit that is incorporated on the back side of the semitransmitting type polarizing plate. Namely, the semitransmitting type polarizing plate is useful for forming a liquid crystal display device of a type that can save the energy of using the light source such as a back light unit in a bright atmosphere and can be used by using an incorporated light source even in a comparatively dark atmosphere.

The elliptic polarizing plate or the circular polarizing plate made by further laminating a retardation plate on a polarizing plate will be described. A retardation plate or the like is used in the case of converting linearly polarized light into elliptically polarized light or circularly polarized light, converting elliptically polarized light or circularly polarized light into linearly polarized light, or changing the polarization direction of linearly polarized light. In particular, as a retardation plate that converts linearly polarized light into circularly polarized light or converts circularly polarized light into linearly polarized light, a so-called ¼ wavelength plate (also referred to as λ/4 plate) is used. A ½ wavelength plate (also referred to as λ/2 plate) is used typically for changing the polarization direction of linearly polarized light.

The elliptic polarizing plate is effectively used for compensating (preventing) the coloring (blue or yellow) generated by birefringence of the liquid crystal layer of a super twist nematic (STN) type liquid crystal display device, so as to perform white and black display without the above-described coloring. Further, those that control the three-dimensional refractive index can compensate (prevent) the coloring generated when the screen of the liquid crystal display device is viewed in an oblique direction, so that it is preferable. The circular polarizing plate is effectively used, for example, for regulating the color tone of the images of the reflection-type liquid crystal display device in which the images are displayed in color, and also has a function of preventing reflection.

Another example thereof is a retardation. As the retardation plate, a birefringent film obtained by monoaxial or biaxial stretching of a polymer material, an oriented film of liquid crystal polymer, one in which the oriented layer of liquid crystal polymer is supported by a film, and the like. The stretching process can be carried out, for example, by roll stretching method, long gap stretching method, tenter stretching method, tubular stretching method, or the like. The magnification of stretching is typically about 1.1 to 3 times in the case of monoaxial stretching. The thickness of the retardation plate is not particularly limited; however, the thickness is typically 10 to 200 μm, preferably 20 to 100 μm.

Examples of the above-described polymer material are polyvinyl alcohol, polyvinyl butyral, polymethyl vinyl ether, polyhydroxyethyl acrylate, hydroxyethylcellulose, hydroxypropylcellulose, methylcellulose, polycarbonate, polyallylate, polysulfone, polyethylene terephthalate, polyethylene naphthalate, polyethersulfone, polyphenylene sulfide, polyphenylene oxide, polyallylsulfone, polyvinyl alcohol, polyamide, polyimide, polyolefin, polyvinyl chloride, cellulose-based polymer, and various two-element or three-element copolymers, graft copolymers, and blended products of these. These polymer materials are made into an oriented product (stretched film) by stretching or the like.

Examples of the above-described liquid crystal polymer are various polymers of main chain type or side chain type in which a conjugate linear atomic group (mesogen) that imparts liquid crystal orientation property is introduced the main chain or the side chain of the polymer. Specific examples of the liquid crystalline polymer of main chain type are, for instance, a polyester-based liquid crystalline polymer having, for example, a nematic orientation property, a discotic polymer, or a cholesteric polymer having a structure such that the mesogen groups are bonded with a spacer part that imparts a bending property. Specific example of a liquid crystal polymer of side chain type are, for instance, those having polysiloxane, polyacrylate, polymethacrylate, or polymalonate as a main chain skeleton and having a mesogen part made of a para-substituted cyclic compound unit having a nematic orientation imparting property via a spacer part made of a conjugate atomic group as the side chain. These liquid crystalline polymers are carried out, for example, by developing a solution of liquid crystalline polymer on an orientation-processed surface of those obtained by a rubbing treatment, tilted vapor deposition of silicon oxide, or the like of the surface of a thin film such as polyimide or polyvinyl alcohol formed on a glass plate, followed by a thermal treatment.

The retardation plate may be a plate having a suitable retardation in accordance with an intended object of use such as various wavelength plates and those intended for compensation of coloring or viewing angle caused by birefringence of the liquid crystal layer, or may be those in which the optical characteristics such as the retardation are controlled by laminating two or more kinds of retardation plates.

The viewing angle compensating film is a film for enlarging the viewing angle so that the images can be looked at comparatively vividly even in a case in which the screen of the liquid crystal apparatus is looked at not vertically to the screen but in a little oblique direction. Examples of such a viewing angle compensating retardation plate are those in which an oriented layer of liquid crystal polymer or the like is supported on an oriented film or a transparent base material such as a retardation film or a liquid crystal polymer. In a typical retardation plate, a polymer film having birefringence that has been monoaxially stretched in the plane direction thereof is used. However, in a retardation plate used as a viewing angle compensating film, a polymer film having birefringence that has been biaxially stretched in the plane direction or a two-direction stretched film such as a polymer film having birefringence with the refractive index controlled in the thickness direction that has been monoaxially stretched in the plane direction and also stretched in the thickness direction or a tilted orientation film is used. Examples of tilted orientation film are those obtained by bonding a heat-shrinking film on a polymer film and performing a stretching process and/or a shrinking process on the polymer film under the action of the shrinking force thereof caused by the heating, or those obtained by oblique orientation of a liquid crystal polymer. The source material polymer of the retardation plate may be one similar to the polymer described in the previous retardation plate, and a suitable source material polymer intended for a purpose such as preventing the coloring or the like caused by change in the viewing angle based on the retardation due to the liquid crystal cell or enlarging the viewing angle can be used.

Also, in view of achieving a wide viewing angle having a good visibility, an optical compensating retardation plate in which an optically anisotropic layer made of an oriented layer of a liquid crystal polymer, particularly a tilted orientation layer of a discotic liquid crystal polymer, is supported by a triacetylcellulose film is preferably used.

A polarizing plate obtained by bonding a polarizing plate with a brightness-improving film is typically used by being disposed on the back side of a liquid crystal cell. The brightness-improving film is a film exhibiting a property of reflecting the linearly polarized light of a predetermined polarization axis or a circularly polarized light of a predetermined direction and transmitting the other light when natural light is incident by a back light unit of a liquid crystal display device or the like or reflection from the back side. The polarizing plate obtained by lamination of a brightness-improving film with a polarizing plate allows light from a light source such as a back light unit to be incident so as to obtain a transmitted light of a predetermined polarization state, and the light other than those in the predetermined polarization state is reflected without being transmitted. The light reflected on this brightness-improving film surface is allowed to be incident again into the brightness-improving film by reversing the light via a reflection layer or the like disposed further in the rear, and a part or a whole thereof is transmitted as the light in the predetermined polarization state, so as to increase the amount of the light that is transmitted through the brightness-improving film, and the polarized light that can be hardly absorbed by the polarizer is supplied so as to increase the amount of light usable for liquid crystal display image display or the like, whereby the brightness can be improved. Namely, in the event that the light is made to be incident through the polarizer from the back side of the liquid crystal cell by a back light unit or the like without using the brightness-improving film, most of the light having a polarization direction that is not coincident with the polarization axis of the polarizer will be absorbed by the polarizer and will not be transmitted through the polarizer. Namely, though differing in accordance with the characteristics of the polarizer to be used, about 50% of the light is absorbed by the polarizer, so that the amount of light that can be used for liquid crystal image display or the like will decrease for that amount, and the images will be dark. The brightness-improving film repeats the process of temporarily reflecting the light having a polarization direction that is liable to be absorbed by the polarizer without allowing the light to be incident into the polarizer and further reflecting the light via a reflection layer or the like disposed further in the rear so as to allow the light to be incident again into the brightness-improving film. Therefore, the brightness-improving film transmits only the light in which the polarization direction of the light that is reflected and reversed between these two has become a polarization direction capable of passing the polarizer, so as to supply the light to the polarizer, whereby the light of the back light unit or the like can be efficiently used for displaying images of the liquid crystal display device, and the screen can be made brighter.

A diffusing plate can be disposed between the brightness-improving film and the above-described reflection layer. The light in the polarization state reflected by the brightness-improving film will proceed towards the above-described reflection layer, and the disposed diffusing layer diffuses the passing light uniformly and eliminates the polarization state so as to achieve a non-polarized state. Namely, the diffusing plate turns the polarized light into the original natural light state. The light in this non-polarized state, namely, the natural light state, repeats the process of proceeding towards the reflection layer or the like, being reflected via the reflection layer or the like, passing through the diffusing plate, and being incident again into the brightness-improving film. By disposing a diffusing plate that turns the polarized light into the original natural light state between the brightness-improving plate and the above-described reflection layer in this manner, the unevenness of the brightness of the display screen can be reduced while maintaining the brightness of the display screen, whereby a uniform and bright screen can be provided. By disposing such a diffusing plate, it seems that the number of repetition of the reflection of the initial light increases to a good amount and, in combination with the diffusing function of the diffusing plate, a uniform and bright screen can be provided.

As the above-described brightness-improving plate, suitable brightness-improving plates such as those exhibiting a property of transmitting the linearly polarized light of a predetermined polarization axis and reflecting the other light such as a multiple-layer thin film of dielectrics or a thin film having a different refractive index anisotropy, or those exhibiting a property of reflecting the circularly polarized light of either one of rightward rotation or leftward rotation and transmitting the other light such as one in which an oriented film of cholesteric liquid crystal polymer or an oriented liquid crystal layer thereof is supported on a film base material.

Therefore, in a type of the above-described brightness-improving film that transmits the linearly polarized light of a predetermined polarization axis, by allowing the transmitted light to be incident as it is into the polarizing plate while arranging the polarization axis, the light can be transmitted efficiently while restraining the absorption loss caused by the polarizing plate. On the other hand, in the brightness-improving film of a type that transmits the circularly polarized light such as a cholesteric liquid crystal layer, the light can be allowed to be incident as it is into the polarizer; however, in view of restraining the absorption loss, the circularly polarized light is preferably allowed to be incident into the polarizer after being converted into linearly polarized light via a retardation plate. Herein, by using a ¼ wavelength plate as the retardation plate, the circularly polarized light can be converted into linearly polarized light.

The retardation plate functioning as the ¼ wavelength plate in a wide wavelength range such as a visible light band can be obtained, for example, by a method of superposing a retardation plate functioning as a ¼ wavelength plate to faint color light of a wavelength of 550 nm and a retardation plate exhibiting a different retardation property, for example, a retardation plate functioning as the ½ wavelength plate. Therefore, the retardation plate to be placed between the polarizing plate and the brightness-improving plate may be made of retardation layers of one layer or two or more layers.

Further, regarding the cholesteric liquid crystal layer, by making a combination of those differing in the reflection wavelength to provide a placement structure in which two or three or more layers are superposed, one can obtain those that reflect circularly polarized light in a wide wavelength range such as a visible light band and, on the basis thereof, a transmitted circularly polarized light in a wide wavelength range can be obtained.

Also, the sheet-shaped product (for example, a polarizing plate) of the present invention may be made of a lamination of a polarizing plate and optical layers of two layers or three or more layers, such as the above-described polarization separating type polarizing plate. Therefore, it may be a reflection-type elliptic polarizing plate or a semitransmitting type elliptic polarizing plate in which the above-described reflection-type polarizing plate or semitransmitting-type polarizing plate is combined with a retardation plate.

An optical film in which the above-described optical layer is laminated on a polarizing plate can be formed by a method of sequentially separately laminating in a production process of the liquid crystal display device; however, an optical film made by lamination in advance is excellent in the stability of the product quality and the assembling work, thereby providing an advantage of improving the production process of the liquid crystal display device. For the lamination, a suitable bonding means such as an adhesive layer can be used. In bonding the above-described polarizing plate with the other optical layers, the optical axes thereof can be in a suitable placement angle in accordance with the retardation property or the like.

In the polarizing plate according to the present invention or the above-described laminated optical members, an adhesive layer for bonding to another member such as a liquid crystal cell is disposed. The adhesive layer is not particularly limited; however, it can be formed with a suitable adhesive agent that accords to the prior art such as an acryl-based adhesive agent. It is preferably an adhesive layer having a low moisture-absorbing property and being excellent in the heat resistance in view of preventing the foaming phenomenon caused by absorption of moisture or a peeling-off phenomenon, preventing decrease in the optical characteristics or warpage of the liquid crystal cell caused by thermal expansion difference or the like, and further a property of forming an image displaying apparatus having a high product quality and being excellent in durability. Also, the adhesive layer may be made to exhibit a light-diffusing property by containing fine particles. The adhesive layer may be disposed on a needed surface in accordance with the needs. For example, referring to a polarizing plate made of a polarizer and a polarizer protective layer, the adhesive layer may be disposed on one surface or on both surfaces of the polarizer protective layer in accordance with the needs.

On the exposed surface of the above-described adhesive layer, a separator (also referred to as a release film) is provisionally attached for covering for the purpose of preventing the contamination thereof until it is subjected to practical use. This can prevent contact with the adhesive layer in an ordinary and usual state of handling. As the separator, one can use a suitable one that accords to the prior art, for example, those in which a suitable thin leaf-like body such as a plastic film, a rubber sheet, paper, cloth, non-woven cloth, a net, a foamed sheet, a metal foil is coated with a suitable release agent such as a silicone-based one, a long-chain-alkyl-based one, a fluorine-based one, or molybdenum sulfide in accordance with the needs, excluding the above-described thickness condition.

On the polarizing plate that is the opposite surface to the surface on which this separator is disposed, a protective film is formed via a weak adhesive agent. The object thereof is mainly for prevention of scars and prevention of contamination. As the protective film, suitably used are protective films according to the prior art, for example, those in which a suitable thin leaf-like body such as a plastic film, a rubber sheet, paper, cloth, non-woven cloth, a net, a foamed sheet, a metal foil is coated with a suitable release agent such as a silicone-based one, a long-chain-alkyl-based one, a fluorine-based one, or molybdenum sulfide in accordance with the needs.

Here, in the present invention, each layer of the polarizer, the polarizer protective film, or the optical film that form the above-described polarizing plate, as well as the adhesive layer, may be made to have, for example, an ultraviolet-absorbing property by a method such as treating with an ultraviolet absorber such as a salicylate-based compound, a benzophenol-based compound, benzotriazol-based compound, cyanoacrylate-based compound, or a nickel-complex-salt-based compound.

The sheet-shaped product of the present invention can be preferably used for forming an image displaying apparatus (corresponding to an optical display device) such as a liquid crystal display device, an organic EL display device, or a PDP.

The polarizing plate or the optical film of the present invention can also be preferably used for forming various apparatus such as a liquid crystal display device. The liquid crystal display device can be formed according to the prior art. Namely, a liquid crystal display device is typically formed by suitably assembling construction components such as a liquid crystal cell (corresponding to an optical display unit), a polarizing plate or an optical film, and an illumination system or the like in accordance with the needs, followed by incorporating a driving circuit. In the present invention, there is no particular limitation except that the polarizing plate or the optical film of the present invention is used, so that it can be carried out according to the prior art. Regarding the liquid crystal cell also, those of any type such as a TN type, an STN type, or a n type can be used, for example.

A suitable liquid crystal display device can be formed such as a liquid crystal display device in which the polarizing plate or the optical film is disposed on one side or on both sides of the liquid crystal cell, or a liquid crystal display device in which a back light unit or a reflection plate is used in an illumination system. In that case, the polarizing plate or the optical film of the present invention can be disposed on one side or on both sides of the liquid crystal cell. In the event that the polarizing plate or the optical film is disposed on both sides, they may be the same or different. Further, in forming the liquid crystal display device, for example, suitable components such as a diffusing plate, an antiglaring layer, a reflection preventive film, a protective plate, a prism array, a lens array sheet, a light-diffusing plate, or a back light unit can be disposed as one layer or as two or more layers at a suitable position.

The sheet-shaped product (for example, a polarizing plate) according to the present invention can be preferably used for forming various apparatus such as a liquid crystal display device. The liquid crystal display device can be formed to have a suitable structure according to the prior art of transmittance type, a reflection type, or a combined type of transmittance and reflection in which the sheet-shaped product (for example, a polarizing plate) according to the present invention is disposed on one side or on both sides of the liquid crystal cell. Therefore, the liquid crystal cell that constitutes the liquid crystal display device is arbitrary and, for example, it may be one that uses a liquid crystal cell of a suitable type such as a simple matrix driving type represented by a thin film transistor type, for example.

Also, in the event that the polarizing plate or the optical member is disposed on both sides of the liquid crystal cell, they may be the same or different. Further, in forming the liquid crystal display device, for example, suitable components such as a prism array sheet, a lens array sheet, a light-diffusing plate, or a back light unit can be disposed as one layer or as two or more layers at a suitable position.

<Construction of Production System>

Embodiment 1

Hereafter, the construction of the defect testing apparatus, the cutting apparatus, the test data processing apparatus, and the production system of the present invention will be described. FIG. 1 is a functional block diagram of the production system. In the functional description of FIG. 1, the means and the like exhibiting the functional effects of the present invention will be mainly described, so that the description of the conventionally known means will be omitted or simplified. The production system of FIG. 1 is constructed to have a defect testing apparatus 10, a first data processing apparatus 20, a slit-cutting apparatus 30, a second test data processing apparatus 40, and a sheet-cutting apparatus 50. Hereafter, each apparatus will be described.

FIG. 2 is a view for describing the whole testing step. The production step is divided into a previous step and a posterior step. The previous step includes (A) a step of processing PVA, (B) a step of processing TAC, (C) a step of bonding PVA and TAC (step of forming a polarizing plate), (D) a step of processing a separator (application of an adhesive agent), (E) a step of processing a protective film (application of an adhesive agent), (F) a step of bonding the polarizing plate to the separator and the protective film, and (G) a step of cutting into slits. In the embodiment 1, the defect testing apparatus is disposed in the steps of (A), (C), (D), and (E).

The posterior step includes (H) a step of cutting into sheets for obtaining a sheet-shaped product provided in separate sheets, and (I) a step of simplified test. An object of the simplified test is directed towards the defects that can be test in a comparatively easy manner, such as scars.

(Defect Testing Apparatus)

The defect testing means can provide a testing section for each production step, for example, for each processing step of a monolayer body constituting the sheet-shaped product or for each laminate body forming (film forming) step. Herein, for the sake of description, the defect detecting means has a polarizer testing section 11, a polarizing plate testing section 12, a separator testing section 13, and a protective film testing section 14. Also, the defect testing means may be constructed only with a polarizing plate testing section 12, or only with a polarizing plate testing section 12, a separator testing section 13 and a protective film testing section 14. Also, it can be constructed in such a manner that, in the step of processing the TAC film constituting the polarizing plate, the defects of the TAC film are tested. By performing the test of defects for each monolayer body (which may contain an adhesive agent or a gluing agent) on the members constituting the sheet-shaped product, the defects can be tested with a good precision without being affected by the separator or the protective film.

Also, by performing the test of defects for each laminate body (for example, the polarizer) constituting the sheet-shaped product, the defects can be tested with a good precision without being affected by the separator or the protective film. Then, regarding the separator and the protective film, the defects are detected for themselves (including the state in which the gluing agent is applied) and, by integrating with other defect information, the defect information can be obtained as a sheet-shaped product in a state in which the separator and the protective film are bonded.

The polarizer testing section 11 is disposed after the drying step of the final stage in the production step of obtaining the polarizer by drying a polyvinyl alcohol (PVA) film subjected to dyeing/crosslinking and stretching process, and tests the defects of a PVA film source. Also, the polarizer testing section 11 can be disposed at a position that can test the PVA before the step of bonding with the TAC.

As a specific testing method, a conventionally known method can be applied. For example, a testing method can be exemplified in which a light source (reflection method or transmittance method) is radiated on both surfaces of a film to capture an image with a CCD camera, and then performing image processing on the obtained image. As a specific apparatus therefor, a known apparatus can be applied. This can detect the foreign substances adhering onto the film surface, the scars, the stains, and the like. Also, a foreign substance that has been kneaded into the film can be detected as well.

Information of the defects obtained in the polarizer testing section 11 is stored together with the position coordinates thereof into the storing section 16. The position coordinates of the defects may be the absolute coordinates of the source, or may be the relative coordinates using as an origin point the position information (or a mark) that has been formed at the end part in the width direction of the source film. The information of the defects is information including a kind, a size, and/or a shape thereof. Also, the information of the defects and the position information thereof (position coordinates) are tied with a string with the identification information (for example, the production lot or the like) of the source film, and are stored into the storing section 16. The position coordinates can be obtained and calculated by a known method, where the amount of transportation from the origin point may be calculated from the transportation speed of the sheet, or the amount of transportation may be sensed using a position sensing device such as a rotary encoder, so as to calculate the coordinates.

Herein, the storing section 16 may be a non-volatile recording medium, or may be a volatile recording medium and, an example is a hard disk.

The polarizing plate testing section 12 is disposed after the bonding step of the final stage in the production step of obtaining the polarizing plate by bonding a triacetylcellulose (TAC) film via an adhesive agent onto both surfaces of the polarizer, and tests the defects of a polarizing plate source. As a specific testing method, a conventionally known method can be applied. For example, a testing method can be exemplified in which a light source (reflection method or transmittance method) is radiated on both surfaces of a film to capture an image with a CCD camera, and then performing image processing on the obtained image. As a specific apparatus therefor, a known one can be applied. Also, a method of testing via a polarization film for testing between the CCD camera and the object of testing can be applied.

As a testing method in the event that the polarizing plate is a laminate body of TAC/PVA/TAC, examples thereof are a method of performing image capturing and image processing by transmitted light or reflected light on both surfaces of the film (systems 1, 2), a method of performing image capturing and image processing by disposing a polarization film for testing between the CCD camera and the object of testing so as to attain a crossed nicol form (which may be referred to as a 0 degree cross) with the polarization axis of the polarizing plate which is the object of testing (system 3), and a method of performing image capturing and image processing by disposing a polarization film for testing between the CCD camera and the object of testing so as to attain a predetermined angle (for example, a range larger than 0 degrees and larger than or equal to 10 degrees) (which may be referred to as an x degree cross) with the polarization axis of the polarizing plate which is the object of testing (system 4).

By the method of image capturing and image processing with the transmitted light, the foreign substances in the inside of the source film can be detected. By the method of image capturing and image processing with the reflected light, the foreign substances adhering to the surface of the source film can be detected. By the method of image capturing and image processing in the 0 degree cross, mainly the surface foreign substances, the stains, and the foreign substances in the inside can be detected as bright points. By the method of image capturing and image processing in the X degree cross, mainly the knicks can be detected.

The information of the defects obtained in the polarization plate testing section 12 is tied with a string with the position information thereof (position coordinates) and the identification information (for example, the production lot or the like) of the source film, and is stored into the storing section 16.

The separator testing section 13 can be disposed after the step of applying an adhesive agent onto the separator. Also, the separator testing section 13 can be disposed at the position where the separator can be tested before bonding with the polarization plate source. As a specific testing method, a conventionally known method can be applied. For example, a testing method can be exemplified in which a light source (reflection method or transmittance method) is radiated on both surfaces of a film to capture an image with a CCD camera, and then performing image processing on the obtained image. As a specific apparatus therefor, a known one can be applied. This can detect foreign substances, stains, scars, poor application of an adhesive agent (streaks or cracks), and the like, which are adhered onto a separator film or an adhesive agent surface. Also, a foreign substance that has been kneaded into the separator film or the adhesive agent can be detected as well.

The information of the defects obtained in the separator testing section 13 is tied with a string with the position information thereof (position coordinates) and the identification information (for example, the production lot or the like) of the source film, and is stored into the storing section 16.

The protective film testing section 14 can be disposed after the step of applying an adhesive agent onto the protective film. Also, the protective film testing section 14 can be disposed at the position where the protective film can be tested before bonding with the polarization plate source. As a specific testing method, a conventionally known method can be applied. For example, a testing method can be exemplified in which a light source (reflection method or transmittance method) is radiated on both surfaces of a film to capture an image with a CCD camera, and then performing image processing on the obtained image. As a specific apparatus therefor, a known one can be applied. This can detect the foreign substances adhering onto the adhesive agent surface, the stains, the scars, the poor application of the adhesive agent (streaks or cracks), and the like. Also, a foreign substance that has been kneaded into the protective film or the adhesive agent can be detected as well.

The information of the defects obtained in the protective film testing section 14 is tied with a string with the position information thereof (position coordinates) and the identification information (for example, the production lot or the like) of the source film, and is stored into the storing section 16.

The defect information preparing section 15 integrates the information of the defects obtained from each testing section, the position information (position coordinates) of the defects and the production identification information that are stored in the storing section 16, and prepares defect information as a sheet-shaped product. For example, since the information of the defects obtained in the polarizer testing section 11 and the information of the defects obtained in the polarizing plate testing section 12 test the same polarizer source, a part of the defect information is duplicated. In this case, if defect information of the same kind, the same size, or the same shape is present at the same position information (position coordinates), it is determined that only one defect is present. Alternatively, for simplification of the data processing, the defect of the same position information (position coordinates) may be determined to be present as only one defect. Also, the defects obtained at the same position can be integrated to include all of them.

Also, in the case of integrating a plurality of the defect information, an origin point is defined, and a process of correcting the position coordinates of the defects using this origin point as a standard is carried out.

The defect information forming section 17 forms the information of the defects obtained in each testing section together with the position information thereof and the product identification information on the object of testing. For example, the above-described information obtained in the polarizer testing section 11 is formed as a code data (two-dimensional code, QR-code) at a predetermined pitch (for example, 1000 mm) on one end surface of the PVA film source. Also, the information obtained in the polarizing plate testing section 12 is formed as a code data (two-dimensional code, QR-code) at a predetermined pitch (for example, 1000 mm) on one end surface of the polarizing plate source.

Also, the defect information forming section 17 can form the defect information prepared in the defect information preparing section 15 (integrated data of the defect information obtained in each testing section) on the protective film or the separator.

The defect information forming section 17 can be constructed with a conventionally known apparatus. For example, in the case of forming a two-dimensional code, the defect information forming section 17 can be constructed with a conventionally known two-dimensional-code-forming apparatus.

The display controlling section 18 functions to allow the test results of each testing section to be displayed on a monitor. Specifically, the display controlling section 18 displays, for example, a size, kind, shape of defects, defect coordinates, and the defect information of the defects together with the production lot and the like on the monitor in real time with the test performed by each testing section. This allows that one can instantly confirm where and how many defects of what sizes are present during the production. For example, when an apparatus operator looks at this monitor, the operator can determine the presence of periodic defects or sporadic defects, and can adjust the inconvenience of that production line, thereby contributing to reduction of the defect creation and an improvement in the yield. Also, since the effective width can be confirmed in real time, it contributes to determination of the product quality of the source.

FIG. 3 is a view showing one example of the defect information displayed on the monitor. The kind (knicks, bright points) and the size (for example, small (<10 μm), middle (10 μm to 20 μm), large (<20 μm)) of the defects together with the width of the source and the coordinate in the longitudinal direction are displayed.

The abnormality determining section 19 determines periodic defects and sporadic defects from the test results of each testing section. Specifically, in accordance with the abnormality determining condition stored beforehand in the storing section 16, the abnormality determining section 19 determines the periodic defects and the sporadic defects. For example, when a predetermined number or more of defects are detected continuously at positions having the same width-direction coordinate (hereafter referred to as x-coordinate) of the source, the abnormality determining section 19 determines that they are periodic defects. Also, when a predetermined number or more of defects are detected continuously at positions having the same longitudinal-direction coordinate (hereafter referred to as y-coordinate) of the source, the abnormality determining section 19 determines that they are sporadic defects.

When abnormality is determined from the result of the abnormality determining section 19, the abnormality determining section 19 preferably functions to issue an alarming sound and/or an alarming display.

(First Test Data Processing Apparatus)

The first test data processing apparatus 20 analyzes the defect information in accordance with a desired set condition and can select, for example, a sheet-shaped product source having the optimum yield. This allows production of a sheet-shaped product source that is optimum for a desired set condition (condition proper to the user side) in the production steps downstream of the slit-cutting step.

The first test data processing apparatus 20 is connected to the defect testing apparatus 10 via a network. The obtaining means 21 can be constructed with known communication means and, in this case, can receive defect information by communication with the communication means (not illustrated) of the defect testing apparatus 10. Also, when the obtaining means 21 is constructed with a recording medium reading means (for example, a CD drive), the defect information may be recorded in the CD. In this case, the defect testing apparatus 10 includes a recording medium writing apparatus (not illustrated), and is constructed to write the defect information. Also, when the obtaining means 21 is constructed with a code data reading apparatus, the obtaining means 21 may be constructed to read the defect information formed on the sheet-shaped product. Also, the first test data processing apparatus 20 may be constructed to receive the defect information that has been read by the later-mentioned slit-cutting apparatus 30.

The defect information obtained by the obtaining means 21 is stored into the storing section 22. The storing section 22 is constructed, for example, with a hard disk.

The yield calculating section 23 obtains defect information from the storing section 22. Then, in accordance with the determination condition which is a condition for determining whether the product is good or bad, the yield calculating section 23 calculates the yield of the sheet-shaped product provided in separate sheets that are obtained by cutting the sheet-shaped product source. One set condition may be provided; however, it is preferably constructed so that a plurality of conditions can be set. This is because this allows that the determination condition of the shipping destination can be suitably selected. Also, it may be constructed in such a manner that the data of the determination condition are stored beforehand in the storing section 22, and the determination condition can be selected from the input receiving means 25, or it may be constructed in such a manner that the determination condition is input directly via the input receiving means 25. Also, in calculating the yield, the yield is preferably calculated by adopting the skip-cut method. In accompaniment with this calculation of the yield, a slit width and/or a slit position is calculated.

For example, in the case of forming a source roll having an effective width by slitting from the size of the sheets and the source width, one source roll having an effective width can be produced by cutting at slit positions of the two sides from one source roll. Here, in consideration of the disposal (position coordinates) of the defects, in the event that the defects are concentrated at one end part, the slit positions can be set so as to avoid the end side having numerous defects. Also, when plural source rolls are obtained from one source roll by slitting, in the case that the defects are concentrated at the center, the slit positions can be set so as to avoid the central part. Also, in obtaining plural source rolls, the individual slit width thereof may be different.

The source setting section 24 (corresponding to the setting means) sets the sheet-shaped product source having a calculated yield being equal to or larger than a predetermined value. For example, when an optimum sheet-shaped product source is desired to be set from a plurality of sheet-shaped product sources, for instance, if the yield is above or equal to the predetermined value, the sheet-shaped product source is set. As the predetermined value, the maximum yield among the plurality of sheet-shaped product sources can be set. When there are data of the shipping destination (or transportation destination in the determination condition, the sheet-shaped product source roll that has been set here will be transported to the shipping destination (or the transportation destination).

As the input receiving means 25, an example can be an input device such as a keyboard, a mouse, or a touch, and in accordance with the operation guidance of the operation screen displayed on a monitor, a setting condition and the like are input.

The display controlling section 26 collectively controls the display such as the operation screen of the first test data processing apparatus 20. Also, the display controlling section 26 can allow the monitor to display the calculated yield. Also, the display controlling section 26 can develop a sheet-shaped product source and display the sheet-shaped product provided in separate sheets obtained as a good product so as to overlap with the developed sheet-shaped product source.

FIGS. 4 to 8 show one example of the display on the yield calculation and the setting of the optimum sheet-shaped product source. FIG. 4 shows an example of the list of the order information from the user and an example of the list of the source lot (sheet-shaped product source lot) that has been already produced. Herein, any of the order information is selected. Next, FIG. 5 is an example of the input screen for inputting the determination condition of the selected order information. In the event that the setting condition is already included in the order information or stored in the storing section 22, the determination condition is automatically input and displayed. The order information includes the size of the sheets and the number of the products to be shipped. As the defect items, there are knicks, bright points, and foreign substances. In the master on the left side of the screen, the lower limit and the upper limit can be set as the defect size standard. When the defects of the lower limit value are more than the defect standard number, the product is determined as bad. When one defect of the upper limit value is present, the product is determined as bad. As the number of defects, the calculation results within the standard and out of the standard are displayed. For example, "378" within the standard shows the number of products that are not dealt with as bad products though defects are present, whereas "12" out of the standard shows the number of products that have been determined as bad products in the defect size standard.

In the simulation on the right side of the screen, one can freely input each item of the defect size standard. For example, when input is made by changing the upper limit to "0.2", the number of defects out of the standard has increased to "20". Namely, on the simulation side, the defect size standard can be freely input, thereby the number of defects which is a result different from the master is calculated, and thus, the comparison with the number of defects in the master can be easily carried out.

FIG. 6 is a different display example showing the master of FIG. 5 and the simulation result. At the center of the screen, the source roll is developed, and the defects out of the standard are shown as square marks. Also, only the defects are shown to avoid the sheet range, and it is shown that the skip cut method is adopted. Also, for the source roll of any lot No., the determination condition of two different kinds of order information is applied and calculated, and is displayed by being separated into upper and lower parts. Herein, it is shown that, from one source roll, two source rolls that accord to two kinds of order information are cut into slits. Also, a lot No., a source length, a source width, a source effective width (slit width), the number of defects, and a yield are displayed. Also, the product number and the standard (identification information) of each order information of the upper developed roll and the lower developed roll, the number of product taken out (number of good products), the slit width, the number of skipping times (number of times the skip cut is made), and the total skip length are displayed. This allows that, for an arbitrary sheet-shaped product source, the setting condition of different order information can be applied at the same time. Also, from one source roll, the yield can be calculated under the setting condition related to plural orders or the same order and, by comparing each, one source roll attaining the optimum yield can be set.

FIG. 7 shows a display example in the case where the source lot of the optimum yield (set lot xxxxx-03, yield 80.3) is set for the order information. The lot No. and the source length are displayed, and the directed destination (shipping destination), the product number, the standard, the size, the scheduled date of shipping, the number of sheets, the number of products taken out, the yield, and the like included in the order information are displayed.

FIG. 8 shows one example in which the defects and the position of taking the sheets are displayed in superposition by developing the source roll. This is one example in which one source roll is slit into two source rolls. For the source width, the effective width is set, and the position of taking the sheets is shown in the effective width thereof. Herein, the position of taking in which sheets of two kinds of sizes are present in mixture. Further, the position of taking is set so as to avoid the defects. This makes the effective width of the source be definite along the entire length. Also, it can be found where and how many the defects of what sizes are present. The outlook state of the total area becomes clear, and the simulation in the state of the position of taking can be made. Also, the accurate source selling price can be decided with the user.

The abnormality determining section 27 determines the periodic defects and the sporadic defects from the defect information of the sheet-shaped product source. Specifically, the abnormality determining section 27 can determine the periodic defects and the sporadic defects in accordance with the abnormality determining condition that is stored beforehand in the storing section 22.

Here, the first test data processing apparatus 20 has been described as a construction obtaining only the defect information of the sheet-shaped product source; however, it can be constructed to be capable of obtaining the information of the defects which are the test results in each testing section and the like. Further, it can be constructed to display the information of the defects in each testing step and to determine the periodic or sporadic defects. Also, the abnormality determining section 27 can be constructed to determine the periodic defects or sporadic defects from the information of the defects in each testing step.

(Slit-Cutting Apparatus)

The slit-cutting apparatus 30 can perform slit-cutting of the sheet-shaped product source that has been set in the first test data processing apparatus 20 in accordance with the slit width and/or the slit position obtained from the first test data processing apparatus 20. Also, when the sheet-shaped product source roll is set and the defect information is read, the slit-cutting apparatus 30 can be constructed to make an inquiry to the first test data processing apparatus 20 about the production lot included in the defect information and to cut into slits in accordance with the slit width and/or the slit position given in response to the inquiry.

The obtaining means 31 can be constructed with known communication means and, in this case, can receive the defect information (defect information of the sheet-shaped product (including the information of defects, position coordinates, and production identification information)), the slit width and/or the slit position due to communication with the first test data processing apparatus 20.

The defect information reading section 32 (corresponding to the defect information reading means) reads the defect information formed on the sheet-shaped product source. In the event that the defect information is formed with code data (for example, QR-code), the defect information reading section 32 can be constructed with a known code data reading apparatus.

The cutting means 33 cuts the sheet-shaped product source into slits by the slit width and/or at the slit position obtained as described above. As this cutting method, a conventionally known slit-cutting method can be applied.

The defect information forming section 34 (corresponding to the defect information forming means) forms defect information at a predetermined position of the sheet-shaped product source that has been cut into slits. For example, as shown in FIG. 9, the defect information is formed as code data (two-dimensional code, QR code) at a predetermined pitch (for example 1000 mm) on one end surface of the sheet-shaped product source after slitting. The defect information includes, for example, the data of the kind, the size, the shape, and the coordinates of the defects as well as the product identification number and the destination of transportation. The defect information forming section 34 can be constructed with a conventionally known apparatus. For example, in the case of forming a two-dimensional code, the defect information forming section 34 can be constructed with a known two-dimensional code forming apparatus. Also, the defect information forming section 34 can form the defect information to include the cutting position information of the sheets. The cutting position information is calculated simultaneously when the yield is calculated in the first test data processing apparatus 20.

(Second Test Data Processing Apparatus)

The production line used in the second test data processing apparatus 40 and the sheet-cutting apparatus 50 may be continuous to the production line located upstream of this; however, they may be disposed at a different line (for example, a different production place). For example, the sheet-shaped product source produced in the upstream production steps may be transported to a different production place, and the downstream production steps may be carried out here. In the downstream production steps, with use of the second test data processing apparatus 40, the optimum sheet-shaped product source is selected while confirming the yield and the like by setting a desired setting condition, so as to produce a sheet-shaped product provided in separate sheets. Also, it can be constructed in such a manner that the cutting position information corresponding to the production identification information is obtained from the first test data processing apparatus 20.

The second test data processing apparatus 40 is connected to the first test data processing apparatus 20 via a network. The obtaining means 41 can be constructed with known communication means and, in this case, can receive defect information (defect information of the sheet-shaped product (including the information of the defects, the position information, the product identification information, and the information of the transportation destination)) by communication with the communication means (not illustrated) of the first test data processing apparatus 20. Also, when the obtaining means 41 is constructed with a recording medium reading apparatus (for example, a CD drive), the defect information may be recorded, for example, in the CD. In this case, the first test data processing apparatus 20 includes a recording medium writing apparatus (not illustrated), and is constructed to write the defect information. Also, when the obtaining means 41 is constructed with a code data reading apparatus, the obtaining means 41 may be constructed to read the defect information formed on the sheet-shaped product source.

The defect information obtained by the obtaining means 41 is stored into the storing section 42. The storing section 42 is constructed, for example, with a hard disk.

The yield calculating means 43 obtains defect information from the storing section 42. Then, in accordance with the determination condition which is a condition for determining whether the product is good or bad, the yield calculating means 43 calculates the yield of the sheet-shaped product provided in separate sheets that are obtained by cutting the sheet-shaped product source. One setting condition may be provided; however, it is preferably constructed so that a plurality of conditions can be set. This is because this allows that the determination condition of the desired determination can be suitably selected. Also, it may be constructed in such a manner that the data of the determination condition are stored beforehand in the storing section 42, and the determination condition can be selected from the input receiving means 45, or it may be constructed in such a manner that the determination condition is input directly via the input receiving means 45. Also, in calculating the yield, the yield is preferably calculated by adopting the skip-cut method. By the skip-cut method, for example, when a defect is present at a position of 20 cm length from the cutting position immediately therebefore in the case of cutting a sheet product having a length of 70 cm, the sheet product is transported and cut so that the cutting may be started, for example, at a position of 21 cm length from the cutting position immediately therebefore by avoiding (skipping) the defect.

The cutting position information preparing section 47 prepares the information on the cutting position of the sheets in accompaniment with the yield calculation. This information of the cutting position includes at least the longitudinal coordinate (y-coordinate) of the source. Then, the information of the cutting position can be supplied to the sheet-cutting apparatus 50.

The source setting section 44 (corresponding to the setting means) sets the sheet-shaped product source having a calculated yield being equal to or larger than a predetermined value. For example, when an optimum sheet-shaped product source is desired to set from a plurality of sheet-shaped product sources, if the yield is above or equal to the predetermined value, the sheet-shaped product source is set. As the predetermined value, the maximum yield among the plurality of sheet-shaped product sources can be set. The sheet-shaped product source roll that has been set here will be transported, for example, to the sheet-cutting apparatus 50 of the next production step.

Examples of the input receiving means 45 are an input device such as a keyboard, a mouse, or a touch panel, whereby a setting condition and the like are input in accordance with the operation guidance of the operation screen displayed on a monitor.

The display controlling section 46 collectively controls the display such as the operation screen of the first test data processing apparatus 40. Also, the display controlling section 46 can allow the monitor to display the calculated yield. Also, the display controlling section 46 can develop a sheet-shaped product source and display the sheet-shaped product provided in separate sheets obtained as a good product so as to overlap with the developed sheet-shaped product source. As described in the first test data processing apparatus 20 shown above, the yield calculation shown in FIGS. 4 to 8 and the setting of the optimum sheet-shaped product source can be displayed.

In addition the second test data processing apparatus 40 has been described as a construction obtaining only the defect information of the sheet-shaped product source; however, it can be constructed to be capable of obtaining the information of the defects which are the test results in each testing section and the like. Further, it can be constructed to display the information of the defects in each testing step and to determine the periodic or sporadic defects.

Further, in the case in which the first test data processing apparatus 20 is allowed to function as a server and the second test data processing apparatus 40 is allowed to function as a client, the functions of the first test data processing apparatus 20 can be constructed with a software program and can be constructed to be capable of being downloaded into the second test data processing apparatus 40. Also, the second test data processing apparatus 40 can be constructed as a client so that the substantial processes may be executed by the first test data processing apparatus 20.

(Cutting Apparatus for Separate Sheets)

The cutting apparatus 50 for separate sheets has a function of cutting the sheet-shaped product source into a sheet-shaped product provided in separate sheets.

The obtaining means 51 can be constructed with known communication means and, in this case, can receive the defect information (defect information of the sheet-shaped product (including the information of defects, position information, and production identification information)) and/or the cutting position information by communication with the communication means (not illustrated) of the second test data processing apparatus 40.

The defect information reading section 52 (corresponding to the defect information reading means) reads the defect information formed on the sheet-shaped product source that has been cut to have a predetermined slit width or on the sheet-shaped product source that has not been subjected to slit cutting. Since the defect information includes position coordinates (x, y), the cutting position can be determined by collating this information with the cutting position information (y coordinate) obtained from the second test data processing apparatus 40. In the event that the defect information is formed with a code data (for example, a QR code), the defect information reading section 52 can be constructed with a known code data reading apparatus.

The cutting means 53 can cut the sheet-shaped product in accordance with the above-described cutting position information. Also, the cutting means 53 can analyze the defect information that has been read, and can produce a sheet-shaped product provided in separate sheets by cutting the sheet-shaped product source in accordance with the determination condition which is a condition for determining whether the product is good or bad. The cutting means 53 may be implemented, for example, by cutting according to the guillotine method, punching-out method, or a laser-cut method.

The product information forming section 54 (corresponding to the product information forming means) forms product information corresponding to the sheet-shaped product on the sheet-shaped product that has been cut into separate sheets. For example, the product information forming section 54 forms product information as a code data (two-dimensional code, QR code) on a part of the sheet-shaped product provided in separate sheets. The product information may include, for example, data such as defect information, production identification number, destination of transportation, and origin of production; however, the production information preferably includes at least the production identification number (production lot). The product information forming section 54 can be constructed with a conventionally known apparatus. For example, in the event of forming a two-dimensional code, the product information forming section 54 can be constructed with a known two-dimensional code forming apparatus.

For example, referring to FIG. 10, the product information is formed sheet by sheet on the sheet-shaped product provided in separate sheets after being cut.

According to the above-described embodiment 1, after the sheet-shaped product is cut into separate sheets, the final determination of good or bad as a product can be made by a simple test of scars or the like. Therefore, there is no need to perform defect testing sheet by sheet or an eye inspection by numerous persons.

Embodiment 2

In the following, the testing function of each step is constructed with an independent testing apparatus; the defect information obtained in each testing apparatus is transmitted to the first test data processing apparatus 120; and the first test data processing apparatus 120 is constructed to prepare the integrated defect information of the sheet-shaped product source.

The polarizer testing apparatus 210 has a construction including a polarizer testing section 211 for testing the defects of the polarizer source, and a communication section 212 that transmits the information on the defects obtained by the test as well as the position information and the production identification information thereof to an external apparatus.

The polarizing plate testing apparatus 220 has a construction including a polarizing plate testing section 221 for testing the defects of the polarizing plate source, and a communication section 222 that transmits the information on the defects obtained by the test as well as the position information and the production identification information thereof to an external apparatus.

The separator testing apparatus 230 has a construction including a separator testing section 231 for testing the defects of the separator, and a communication section 232 that transmits the information on the defects obtained by the test as well as the position information and the production identification information thereof to an external apparatus.

The protective film testing apparatus 240 has a construction including a protective film testing section 241 for testing the defects of the protective film, and a communication section 242 that transmits the information on the defects obtained by the test as well as the position information and the production identification information thereof to an external apparatus.

The first test data processing apparatus 120 is constructed to include a communication section 121 that receives information on the defects, position information thereof, and product identification information from each testing apparatus, a storing section 122 that stores the received information on the defects, position information thereof, and product identification information in association, a defect information preparing section 128 that prepares the defect information of the sheet-shaped product source by integrating the information on the defects, position information thereof, and product identification information received from each testing apparatus, a yield calculating section 123 for analyzing the defect information and calculating the yield of the sheet-shaped product provided in separate sheets obtained by cutting the sheet-shaped product source in accordance with a determination condition which is a condition for determining whether the product is good or bad, and a source setting section 124 that sets a sheet-shaped product source in which the yield is above or equal to a predetermined value.

Among the constituent elements illustrated herein, description for elements having the same function as those described in embodiment 1 will be omitted.

In the embodiment 2, the first test data processing apparatus 120 is equipped with a defect information preparing section 128. The substantial function of the defect information preparing section 128 is the same as the one described in the embodiment 1, and can integrate the information on the defects detected in each testing apparatus and can prepare defect information as the sheet-shaped product source.

Also, the first test data processing section 120 transmits a command signal (which may include the defect information; in the event that it does not include the defect information, the defect information is received from the testing apparatus) for forming the detected defect information to the code forming apparatus (corresponding to the defect information forming means) disposed in the neighborhood of each testing apparatus. By this command signal, the code forming apparatus forms defect information at a predetermined position. Also, the first test data processing apparatus can control the monitor so as to allow the monitor to display the defect information so as to interlock with the test of the testing apparatus (depending on the function of the display controlling section 126). Also, when abnormality is determined in the abnormality determining section, the first test data processing apparatus 120 can perform warning display showing the presence of abnormality on the monitor of the corresponding testing apparatus (this depends on the function of the abnormality determining section 127).

Embodiment 3

In the embodiment 3, description will be given on a mode in which one test data processing apparatus is present. In the embodiments 1 and 2, it is so constructed that two test data processing apparatus are present. However, when the place of production is the same, the test data processing apparatus can be constructed with one apparatus.

In such a case, the first test data processing apparatus may be constructed to be equipped with the function of the cutting position information preparing section, and the cutting apparatus for slitting may analyze the read defect information, calculate the cutting position in accordance with a determination condition which is a condition for determining whether the product is good or bad, and produce the sheet-shaped product provided in separate sheets by cutting the sheet-shaped product source.

Embodiment 4

The first test data processing apparatus and the second test data processing apparatus of the present invention can be realized by collaborating action of software and hardware (CPU, memory, and the like), and can be realized with an exclusive-use circuit, a firm ware, and the like, or a combination thereof.

In realizing with software, the program thereof will be as follows. This program is recorded in a recording medium and can be provided as a recording medium, and may be provided (providing by downloading) via a communication line. In the event of providing via the communication line, a part of the function thereof may be provided and the other part may remain in the server, so that it will be comprised within the technical scope of the present invention as long as the function of the present invention is exhibited as a whole function.

A software program of the present invention is a program for allowing a computer to execute the steps of:

receiving input of a determination condition which is a condition for determining whether a product is good or bad;

obtaining defect information related to defects obtained by testing a monolayer body and/or a laminate body constituting a sheet-shaped product having at least an optical film which is a member of an optical displaying apparatus in a state in which a protective layer on a surface of the sheet-shaped product is not disposed;

analyzing the defect information and calculating a yield according to the determination condition; and allowing displaying means to display the calculated yield.

Another software program of the present invention is a program for allowing a computer to execute the steps of:

obtaining defect information detected by defect detecting means for detecting defects of a monolayer body and/or a laminate body constituting a sheet-shaped product having at least an optical film which is a member of an optical displaying apparatus in a state in which a protective layer on a surface of the sheet-shaped product is not disposed;

analyzing the obtained defect information and calculating a yield of the sheet-shaped product provided in separate sheets obtained by cutting a sheet-shaped product source according to a determination condition which is a condition for determining whether a product is good or bad; and setting a sheet-shaped product source in which the yield is above or equal to a predetermined value.

Another Embodiment

The present invention has been described with respect to a sheet-shaped product including a polarizing plate; however, the present invention is not limited to this and can be applied to a laminate body of a polarizing plate and a retardation plate or to a retardation plate alone as an optical film.

What is claimed is:

1. A production system for producing a sheet-shaped product including an optical film for producing a sheet-shaped product having at least an optical film which is a member of an optical displaying apparatus, comprising:
- defect detecting means for detecting defects of a monolayer film and/or a laminate film constituting the sheet-shaped product in a state in which a protective layer film on a surface of the sheet-shaped product is not disposed;
- defect information preparing means for preparing defect information which is information related to the defects detected by said defect detecting means;
- yield calculating means for analyzing the defect information prepared in said defect information preparing means, and calculating a cutting position and calculating a yield of the sheet-shaped product provided in separate sheets obtained by cutting the sheet-shaped product source according to a determination condition which is a condition for determining whether the product is good or bad;
- setting means for setting a sheet-shaped product source in which said yield is above or equal to a predetermined value;
- first cutting means for cutting said set sheet-shaped product source with a slit width;
- defect information forming means for forming defect information on the protective layer of said cut sheet-shaped product source;
- defect information reading means for reading the defect information formed by said defect information forming means; and
- second cutting means for analyzing the defect information that is read by said defect information reading means, and producing a sheet-shaped product provided in separate sheets by cutting the sheet-shaped product source according to a determination condition which is a condition for determining whether the product is good or bad.

2. The production system for producing a sheet-shaped product of claim 1, further comprising product information forming means for forming product information corresponding to the sheet-shaped product on said cut sheet-shaped product provided in separate sheets.

3. A test data processing apparatus comprising:
- input receiving means for receiving input of a determination condition which is a condition for determining whether a product is good or bad;
- defect information obtaining means for obtaining defect information related to defects obtained by testing a monolayer film and/or a laminate film constituting a sheet-shaped product having at least an optical film which is a member of an optical displaying apparatus in a state in which a protective layer film on a surface of the sheet-shaped product is not disposed;
- yield calculating means for analyzing said defect information and calculating a yield according to said determination condition; and
- display controlling means for controlling so as to allow displaying means to display said calculated yield;
- wherein said display controlling means develops a sheet-shaped product source and controls so as to display the sheet-shaped product provided in separate sheets obtained as a good product so as to overlap with the developed sheet-shaped product source.

* * * * *